US010183965B2

(12) United States Patent
Neely et al.

(10) Patent No.: US 10,183,965 B2
(45) Date of Patent: Jan. 22, 2019

(54) COFACTOR ANALOGUES FOR METHYLTRANSFERASES

(71) Applicant: KATHOLIEKE UNIVERSITEIT LEUVEN, Leuven (BE)

(72) Inventors: Robert Neely, Birmingham (GB); Volker Leen, Kortenaken (BE); Johan Hofkens, Oud-Heverlee (BE)

(73) Assignee: KATHOLIEKE UNIVERSITEIT LEUVEN, Leuven (BE)

( * ) Notice: Subject to any disclaimer, the term of this patent is extended or adjusted under 35 U.S.C. 154(b) by 0 days.

(21) Appl. No.: 15/507,628

(22) PCT Filed: Aug. 31, 2015

(86) PCT No.: PCT/EP2015/069879
§ 371 (c)(1),
(2) Date: Feb. 28, 2017

(87) PCT Pub. No.: WO2016/030546
PCT Pub. Date: Mar. 3, 2016

(65) Prior Publication Data
US 2017/0283453 A1    Oct. 5, 2017

(30) Foreign Application Priority Data

Aug. 29, 2014  (GB) .................................. 1415349.8

(51) Int. Cl.
| C07H 19/16 | (2006.01) |
| C07H 19/167 | (2006.01) |
| C12N 9/10 | (2006.01) |
| C12Q 1/6876 | (2018.01) |

(52) U.S. Cl.
CPC ........... *C07H 19/16* (2013.01); *C07H 19/167* (2013.01); *C12N 9/1007* (2013.01); *C12Q 1/6876* (2013.01); *C12Y 201/01072* (2013.01); *C12Q 2600/154* (2013.01)

(58) Field of Classification Search
None
See application file for complete search history.

(56) References Cited

U.S. PATENT DOCUMENTS 8,008,007 B2    8/2011  Weinhold et al.

FOREIGN PATENT DOCUMENTS

| EP | 1874790 A2 | 1/2008 |
| WO | 8810315 A1 | 12/1988 |
| WO | 8909622 A1 | 10/1989 |

OTHER PUBLICATIONS

STN Registry 1485440-63-8. Entered Dec. 2, 2013.*
Borchardt et al., "Potential Inhibitors of S-Adenosylmethionine-Dependent Methyltransferases. 4. Further Modifications of the Amino Acid and Base Portions of S-Adenosyl-L-Homocysteine," Journal of Medicinal Chemistry, Jan. 1, 1976, pp. 1094-1099, vol. 19, No. 9.
Erlich, "PCR Technology, Principles and Applications for DNA Amplification", M Stock Press, 1989, 246 Pages.
Erlich, "Polymerase Chain Reaction", Journal of Clinical Immunology, vol. 9, No. 6, 1989, pp. 437-447.
Galfre et al., "Preparation of Monoclonal Antibodies: Strategies and Procedures", Methods in Enzymology, vol. 73, 1981, pp. 3-46.
Graham et al., "DNA Sequencing Protocols", Methods in Molecular Biology, Humana Press Inc. Second Edition, vol. 167, 2001, 222 Pages.
Hemdan et al., "Development of Immobilized Metal Affinity Chromatography", Journal of Chromatography, vol. 323, 1985, pp. 255-264.
Innis et al., "PCR Protocols, A guide to Methods and Applications", Academic Press, Inc., 1990, 482 Pages.
International Search Report for corresponding International PCT Application No. PCT/EP2015/069879, dated Dec. 3, 2015.
Isalm et al., "Defining Efficient Enzyme-Cofactor Pairs for Bioorthogonal Profiling of Protein Methylation," PNAS, Oct. 15, 2013, pp. 16778-16783, vol. 110, No. 42.
Kagan et al., "Widespread Occurrence of Three Sequence Motifs in Diverse S-Adenosylmethionine-Dependent Methyltransferases Suggests a Common Structure for These Enzymes", Archives of Biochemistry and Biophysics vol. 310, No. 2, May 1, 1994, pp. 417-427.
Kohler et al., "Continuous Cultures of Fused Cells Secreting Antibody of Predefined Specificity", Nature, vol. 256, Aug. 7, 1975, pp. 495-497.
Kwoh et al., "Transcription-Based Amplification System and Detection of Amplified Human Immunodeficiency Virus Type 1 with a Bead-Based Sandwich Hybridization Format", Proc. Natl. Acad. Sci. USA, vol. 86, Feb. 1989, pp. 1173-1177.
Lukinavicius et al., "Engineering the DNA Cytosine-5 Methyltransferase Reaction for Sequence-Specific Labeling of DNA," Nucleic Acids Research, Oct. 5, 2012, pp. 11594-11602, vol. 40, No. 22.
Malmborg et al., "BIAcore as a Tool in Antibody Engineering", Journal of Immunological Methods, vol. 183, 1995, pp. 7-13.
Porath et al., Metal Chelate Affinity Chromatography, A New Approach to Protein Fractionation, Nature, vol. 258, Dec. 18, 1975, pp. 598 and 599.
Pignot et al., "Efficient Synthesis of S-Adenosyl-L-Homocysteine Natural Product Analogues and Their Use to Elucidate the Structural Determinant for Cofactor Binding of the DNA Methyltransferase M.Hhal", Eur. J. Org. Chem., 2000, pp. 549-555.

(Continued)

*Primary Examiner* — Deepak R Rao
*Assistant Examiner* — Laura M Daniel
(74) *Attorney, Agent, or Firm* — Workman Nydegger

(57) ABSTRACT

Cofactor analogs for methyltransferases are disclosed. The compounds are represented by formula (I) wherein R1 is COOH or COO—; X is an organic or inorganic anion carrying one or more negative charges; Y and Y' are H, or an alkyl; R2 is $NH_2$, NHBoc, or H; and Z is S or Se. R comprises a carbon-carbon double bond, carbon-oxygen double bond, carbon-sulfur double bond, carbon-nitrogen double bond, a carbon-carbon triple bond, carbon-nitrogen triple bond, an aromatic carbocyclic or heterocyclic system in β-position to the sulfonium center, unsaturated c-c bond, or c-heteroatom bond where the heteroatom is O, N, S.

20 Claims, 3 Drawing Sheets

(56) References Cited

OTHER PUBLICATIONS

Pljevaljcic et al., "Sequence-Specific DNA Labeling Using Methyltransferase," Methods in Molecular Biology, Jan. 1, 2004, pp. 145-161, vol. 283.
Porath et al., "Cascade-mode Multiaffinity Chromatography, Fractionation of Human Serum Proteins", Journal of Chromatography, vol. 550, 1991, pp. 751-764.
Porath et al., "Immobilized Metal Ion Affinity Chromatography", Protein Expression and Purification, vol. 3, 1992, pp. 263-281.
Schlenk et al., "The S-n-Propyl Analogue of S-Adenosylmethionine," Biochimica et Biophysics Acta, Jan. 1, 1975, pp. 312-323, vol. 385.
Schier et al., "Efficient in vitro Affinity Maturation of Phage Antibodies Using BlAcore Guided Selections", Hum. Antibod. Hybridomas, vol. 7, No. 3, 1996, pp. 97-105.
Schmidt et al., "The Random Peptide Library-Assisted Engineering of a C-Terminal Affinity Peptide, Useful for the Detection and Purification of a Functional Ig Fv Fragment", Protein Engineering, vol. 6, No. 1, 1993, pp. 109-122.
Urano et al., "Evolution of Fluorescein as a Platform for Finely Tunable Fluorescence Probes", JACS Articles, Mar. 10, 2005, J. Am. Chem. Soc., vol. 127, pp. 4888-4894.
Walker et al., "Strand Displacement Amplification—an Isothermal, in vitro DNA Amplification Technique", Nucleic Acids Research, vol. 20, No. 7, 1992, pp. 1691-1696. Islam et al., "Defining Efficient Enzyme-Cofactor Pairs for Bioorthogonal Profiling of Protein Methylation," Proceedings of the National Academy of Sciences of the United States of America, vol. 110, No. 42, Oct. 25, 2013, pp. 16778-16783.
Islam et al., "Supporting Information for Defining Efficient Enzyme-Cofactor Pairs for Bioorthogonal Profiling of Protein Methylation," Proceedings of the National Academy of Sciences of the United States of America, vol. 110, No. 42, Oct. 25, 2013, 114 Pages.

\* cited by examiner

COFACTOR ANALOGUES FOR METHYLTRANSFERASES

TECHNICAL FIELD OF THE INVENTION

The present invention relates to co-factor analogues for catalysis reactions involving methyltransferases, as well as the targeted modification of proteins and polynucleotides (DNA and RNA) using a methyltransferase-catalysed transfer of a chemical group, tag or label from a synthetically prepared cofactor analogue to the biomolecule of interest.

BACKGROUND OF THE INVENTION

Enzymes are the workhorses of our cells. Part of the key to their success is that they are able to provide supreme substrate specificity in such a chemically complex environment. Such specificity has evolved over millennia and, as such, these enzymes provide a remarkable tool for performing all manner of chemical tasks.

One group of enzymes, the methyltransferases, have evolved to catalyse the transfer of a methyl group from a small molecule cofactor, s-adenosyl-L-methionine (also called "SAM" or "AdoMet"), to a range of biomolecular targets including DNA, RNA and other proteins and enzymes. In the cell, methyltransferase-catalysed modification plays a host of important roles, such as gene regulation, and understanding of the methylation status of DNA is now a burgeoning scientific field (epigenetics).

In order to develop novel technologies based on the specific and covalent modification of biomolecular substrates by the methyltransferase enzymes, several research groups have recently developed synthetic analogues of the AdoMet cofactor. The co-factors have primarily been used with DNA methyltransferases.

Broadly, there are two classes of AdoMet: (1) aziridine derivative cofactors and (2) the so-called 'mTAG' cofactors carrying extended chemical chains in place of a methyl group. Unfortunately, both classes have limitations. For example, the DNA methyltransferases are unable to turn-over the aziridine derivative cofactors, meaning that stoichiometric amounts of cofactor and enzyme are required for complete substrate modification. Further, multiple enzymes have been screened for activity with these cofactors, but only a few show significant activity, perhaps due to the relatively bulky chemical structure of the aziridine analogues.

There are many reported variants of the mTAG cofactors. Examples of variants of mTAG cofactors are described in EP1874790B1. However, their synthesis is challenging and, critically, the yield of the final step of the synthesis (coupling of the transferable group to the cofactor) is low and requires the presence of several tens- to hundreds- of fold excess of the transferable moiety. This means that, for example, the coupling of a fluorophore directly to the mTAG cofactor is prohibitively expensive and scale-up to quantities of commercial relevance is challenging. Thus, there remains a need in the art for new cofactors which may be readily used with a variety of DNA methyltransferases, and for which the synthesis is straightforward and scalable.

SUMMARY OF INVENTION

It is an object of the present invention to provide good cofactors for use with methyltransferases enzymes.

It is an advantage of embodiments of the present invention that the cofactorsresemble the mTAG cofactorsstructurally and functionally, but display more favorable properties, such as for example full scalability of synthesis with improved yields and minimum number of intermediate steps. It is an advantage of embodiments of the present invention that a flexible synthetic approach to a cofactor analogue is obtained that opens up a range of new approaches for methyltransferase-directed biomolecule modification. It is an advantage of embodiments of the present invention that an improved behavior of this new generation of cofactors is obtained when compared to the mTag cofactors, in both enzyme specificity and efficiency, efficiency of diastereomer purification and reactivity of the diastereoisomers.

In this new generation of cofactors, the naturally occurring homocysteine group found in the amino acid portion of the Adomet cofactor has been replaced by a cysteine. According to the scientific literature, such a molecule should not be functional (Borchardt et al., J. Med. Chem., 1976, 1104). In an assay for competitive binding to various methyltransferases, Borchardt et al. concluded that a "three-carbon distance between the terminal groups and the sulfonium center [as seen in the naturally occurring homocysteine group] are absolute requirements for the proper binding of the molecule" (page 1107, column 1, $2^{nd}$ paragraph), because an analogue with a cysteine group did not inhibit binding of a test substrate to methyltransferases, in contrast to inhibition by analogues with homocysteine groups. Thus, a surprising effect of the disclosed cofactors is that they not only bind to methyltransferases but also participate in transfer of larger groups and labeling of biomolecules.

One aspect of the present disclosure relates to a compound represented by formula (I):

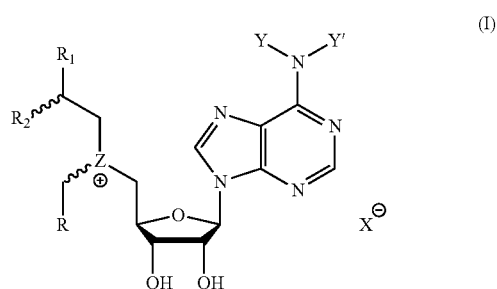

wherein
R1 is COOH or COO—;
X is an organic or inorganic anion carrying one or more negative charges;
Y and Y' are H, or an alkyl;
Z is S or Se
R2 is $NH_2$, NHBoc, or H; and
R comprises a carbon-carbon double bond, carbon-oxygen double bond, carbon-sulfur double bond, carbon-nitrogen double bond, a carbon-carbon triple bond, carbon-nitrogen triple bond, an aromatic carbocyclic or heterocyclic system in β-position to the sulfonium center, unsaturated c-c bond, or c-heteroatom bond where the heteroatom is O, N, S. It was surprisingly found that in embodiments according to the present invention compounds are provided that comprise cysteine, and e.g. not homocysteine, whereby the compounds obtained still provide functionality for methyl transferases. It is an advantage of embodiments of the present invention that such compounds can be produced with high efficiency. It is an advantage of embodiments of the present invention that products are obtained that can be used as cofactors, whereby the synthesis is more easy to perform, e.g. has a higher yield. It is an advantage of embodiments according to the present invention that the obtained products are more easy to separate in their enantiomers. It is an advantage of embodiments of the present invention that both enantiomers can be active.

It is an advantage of embodiments of the present invention that the products obtained can especially advantageously be used for certain enzymes, for which cofactors e.g. based on homocysteines, are operating less accurately.

In the compound, the R, R2, Y, and Y' may be selected from the following:

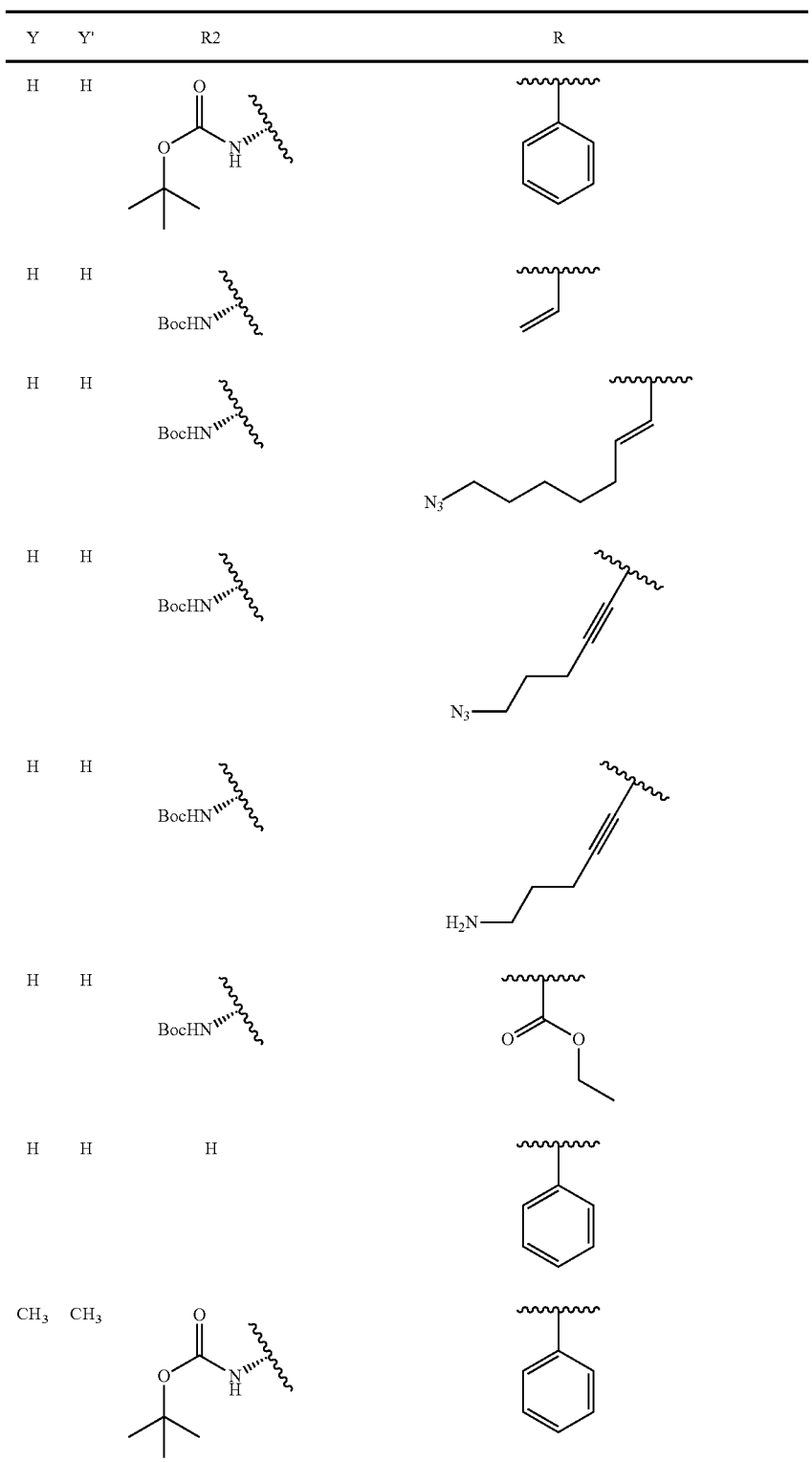

-continued
| Y | Y' | R2 | R |
|---|---|---|---|
| H | H | 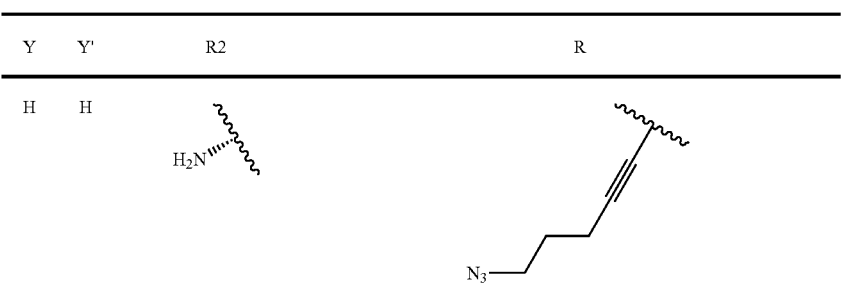 | |
| H | H | 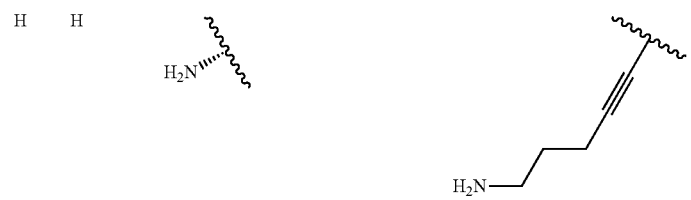 | |
| H | H | 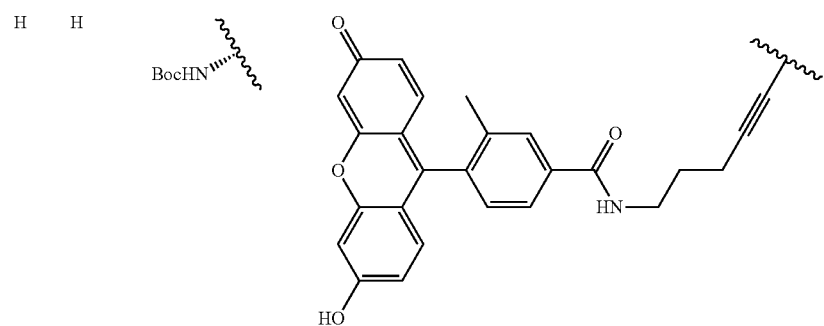 | |
| H | H | H | 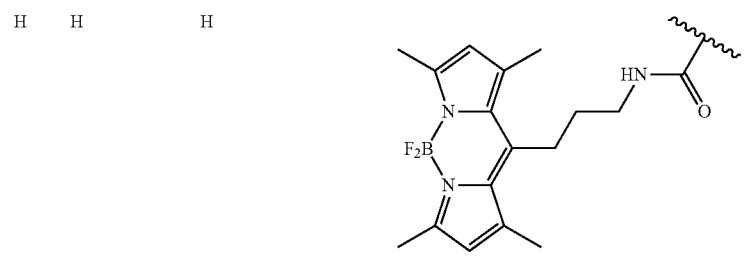 |

-continued
| Y | Y' | R2 | R |
|---|----|----|---|
| H | H | NH2 | 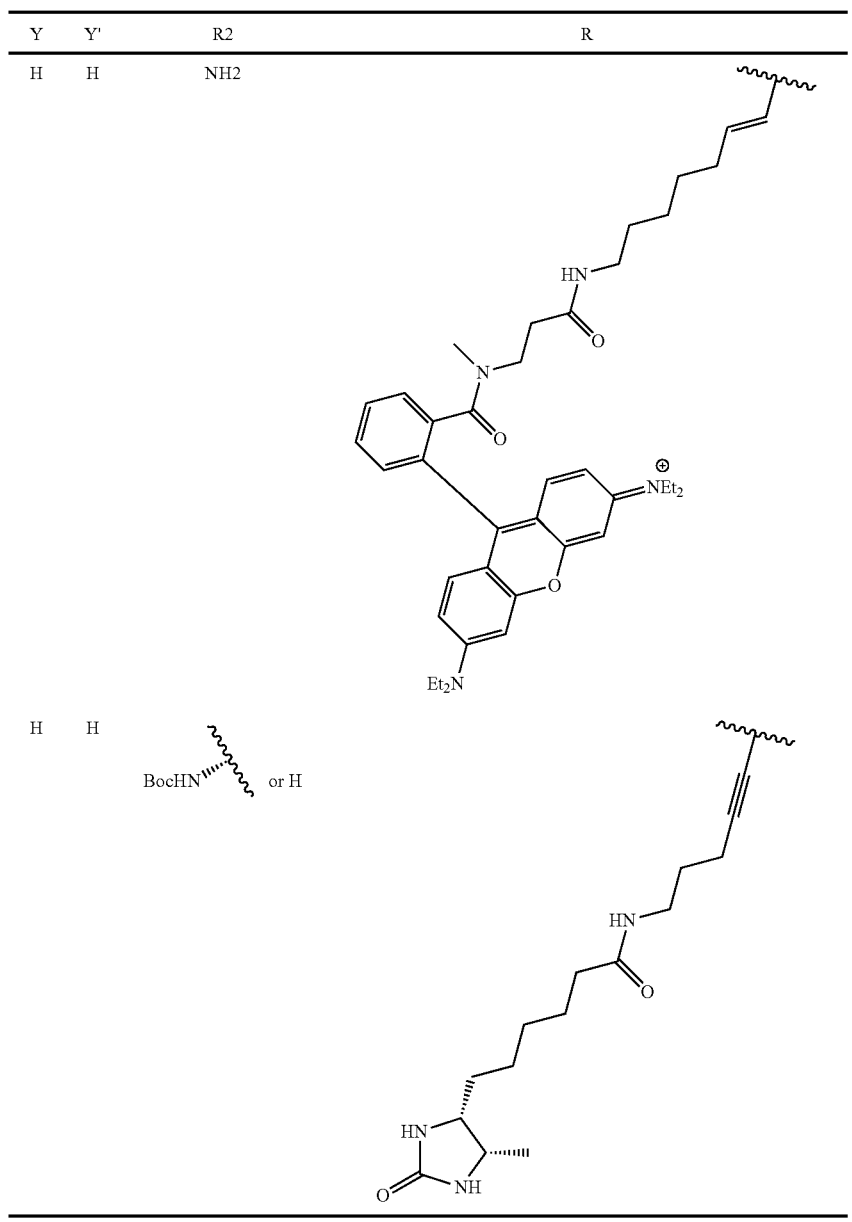 |
| H | H | ![BocHN structure] or H | |
In some embodiments, the compound is selected from the group comprising:
| Compound | Name |
|----------|------|
| 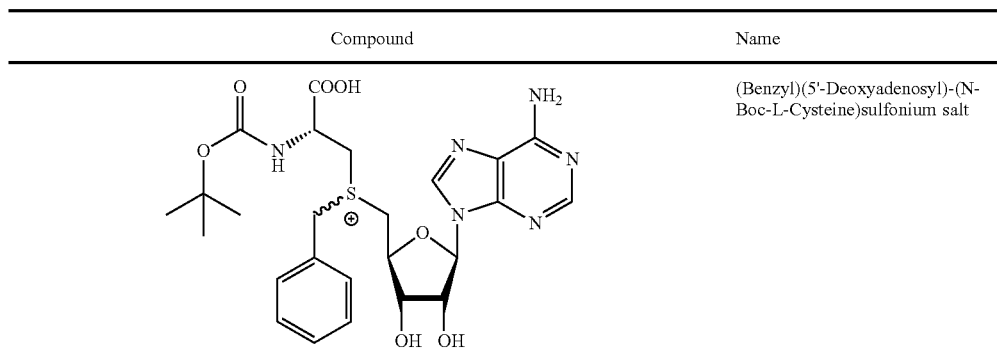 | (Benzyl)(5'-Deoxyadenosyl)-(N-Boc-L-Cysteine)sulfonium salt |

-continued

| Compound | Name |
|---|---|
| | (Allyl)(5'-Deoxyadenosyl)-(N-Boc-L-Cysteine)sulfonium salt |
| | (8-Azido-oct-2-ene)(5'-Deoxyadenosyl)-(N-Boc-L-Cysteine)sulfonium salt |
| | (6-Azido-hex-2-yne)(5'-Deoxyadenosyl)-(N-Boc-L-Cysteine)sulfonium salt |
| | (6-Amino-hex-2-yne)(5'-Deoxyadenosyl)-(N-Boc-L-Cysteine)sulfonium salt |
| | (Ethyl Carboxymethyl)(5'-Deoxyadenosyl)-(N-Boc-L-Cysteine)sulfonium salt |

-continued

| Compound | Name |
|---|---|
| | (Benzyl)(5'-Deoxyadenosyl)-(3-Propionate)sulfonium salt |
| | (Benzyl)(5'-Deoxy-$N^6$,$N^6$-dimethyladenosyl)-(N-Boc-L-Cysteine) sulfonium salt |
| | (6-Azido-hex-2-yne)(5'-Deoxyadenosyl)-(L-Cysteine)sulfonium salt |
| | (6-Amino-hex-2-yne)(5'-Deoxyadenosyl)-(L-Cysteine)sulfonium salt |

| Compound | Name |
|---|---|
| (structure) | Fluorescent sulfonium salt |
| (structure) | Fluorescent sulfonium salt II |
| (structure) | Fluorescent sulfonium salt III |

| Compound | Name |
| --- | --- |
| 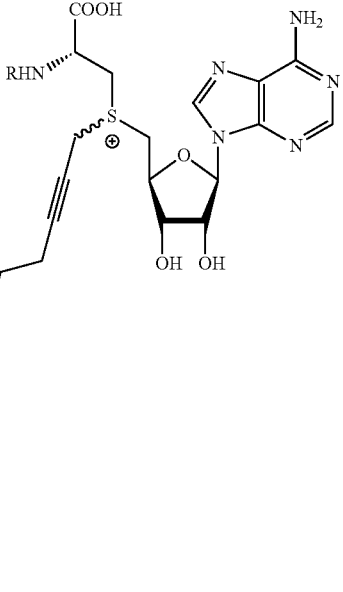 | Dethiobiotin sulfonium cofactor |

In one aspect the present invention also relates to a complex of a compound as described above and a methyltransferase capable of using S-adenosyl-L-methionine (SAM or AdoMet) as a cofactor.

The present invention furthermore relates to a kit comprising a compound (I) as described above, or a complex as described above, packed in a container.

The present invention furthermore relates to a pharmaceutical or diagnostic composition comprising a compound as described above or a complex as described above.

The present invention also relates to a method for the preparation of a modified target molecule, the method comprising the incubation of the target molecule with a compound (I) as described above in the presence of a methyltransferase which is capable of using the compound (I) as a cofactor and under conditions which allow for the transfer of part of the compounds onto the target molecule. This may for example require incubating the methyltranseferase enzyme with a compound as described above in a suitable aqueous buffered solution for the appropriate time, followed by a purification of the substrate, which usually comprises proteinase treatment of the sample followed by purification through chromatography or precipitation.

The present invention also relates to a method for detecting sequence-specific methylation in a biomolecule, comprising:
(a) contacting a biomolecule with an S-adenosyl-L-methionine-dependent methyltransferase in the presence of a detectable cofactor of said methyltransferase; and
(b) detecting whether the recognition site of said methyltransferase has been modified with the cofactor or a derivative thereof, wherein modification of the recognition site of said methyltransferase is indicative of an absence of methylation at said recognition site, wherein said cofactor is a compound of formula (I) as described above.

The present invention furthermore relates to a method for synthesizing a compound as described above, the method comprising coupling a thioether with a lactone. It is an advantage of embodiments of the present invention that the cofactors can be made with high efficiency, compared to at least some known prior art cofactors.

Particular and preferred aspects of the invention are set out in the accompanying independent and dependent claims. Features from the dependent claims may be combined with features of the independent claims and with features of other dependent claims as appropriate and not merely as explicitly set out in the claims.

These and other aspects of the invention will be apparent from and elucidated with reference to the embodiment(s) described hereinafter.

Figure 1:
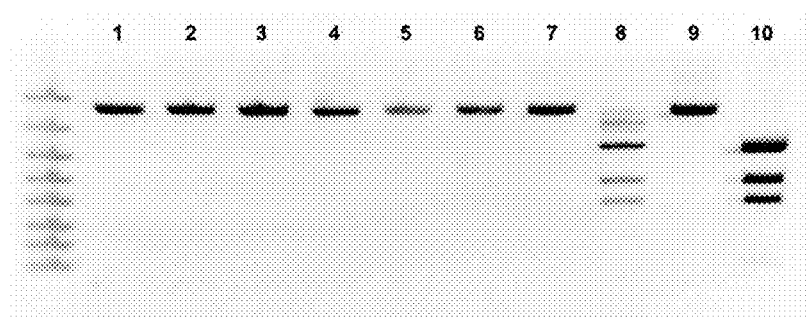
FIG. 1 shows the image of agarose gel, illustrating how incubation of DNA with adenosine methyltransferase enzyme (M.TaqI) and a synthetic cofactor results in the same protection as with the natural cofactor, against cutting by a restriction enzyme.
Figure 2:
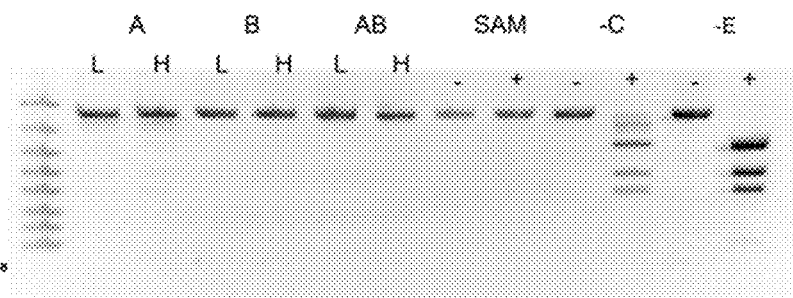
FIG. 2 shows the image of agarose gel, illustrating how incubation of DNA with adenosine methyltransferase enzyme (M.TaqI) and both diastereoisomers of a synthetic cofactor results in the same protection as with the natural cofactor, against cutting by a restriction enzyme, and with no difference between the diastereoisomers.

The drawings are only schematic and are non-limiting. In the drawings, the size of some of the elements may be exaggerated and not drawn on scale for illustrative purposes.

DETAILED DESCRIPTION OF INVENTION

The present invention will be described with respect to particular embodiments and with reference to certain drawings but the invention is not limited thereto but only by the claims. Furthermore, the terms first, second and the like in the description and in the claims, are used for distinguishing between similar elements and not necessarily for describing a sequence, either temporally, spatially, in ranking or in any other manner. It is to be understood that the terms so used are interchangeable under appropriate circumstances and that the embodiments of the invention described herein are capable of operation in other sequences than described or illustrated herein.

It is to be noticed that the term "comprising", used in the claims, should not be interpreted as being restricted to the means listed thereafter; it does not exclude other elements or steps. It is thus to be interpreted as specifying the presence of the stated features, integers, steps or components as referred to, but does not preclude the presence or addition of one or more other features, integers, steps or components, or groups thereof. Thus, the scope of the expression "a device comprising means A and B" should not be limited to devices consisting only of components A and B. It means that with respect to the present invention, the only relevant components of the device are A and B.

Reference throughout this specification to "one embodiment" or "an embodiment" means that a particular feature, structure or characteristic described in connection with the embodiment is included in at least one embodiment of the present invention. Thus, appearances of the phrases "in one embodiment" or "in an embodiment" in various places throughout this specification are not necessarily all referring to the same embodiment, but may. Furthermore, the particular features, structures or characteristics may be combined in any suitable manner, as would be apparent to one of ordinary skill in the art from this disclosure, in one or more embodiments.

Similarly it should be appreciated that in the description of exemplary embodiments of the invention, various features of the invention are sometimes grouped together in a single embodiment, figure, or description thereof for the purpose of streamlining the disclosure and aiding in the understanding of one or more of the various inventive aspects. This method of disclosure, however, is not to be interpreted as reflecting an intention that the claimed invention requires more features than are expressly recited in each claim. Rather, as the following claims reflect, inventive aspects lie in less than all features of a single foregoing disclosed embodiment. Thus, the claims following the detailed description are hereby expressly incorporated into this detailed description, with each claim standing on its own as a separate embodiment of this invention.

Furthermore, while some embodiments described herein include some but not other features included in other embodiments, combinations of features of different embodiments are meant to be within the scope of the invention, and form different embodiments, as would be understood by those in the art. For example, in the following claims, any of the claimed embodiments can be used in any combination.

In the description provided herein, numerous specific details are set forth. However, it is understood that embodiments of the invention may be practiced without these specific details. In other instances, well-known methods, structures and techniques have not been shown in detail in order not to obscure an understanding of this description.

One aspect of the present disclosure is a compound of formula (I):

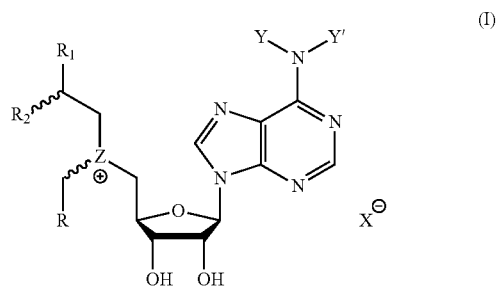

wherein

R1 is COOH or COO—

X is an organic or inorganic anion carrying one or more negative charges; and

Y and Y' are H, or an alkyl;

R2 is $NH_2$, NHBoc, or H;

R comprises a carbon-carbon double bond, carbon-oxygen double bond, carbon-sulfur double bond, carbon-nitrogen double bond, a carbon-carbon triple bond, carbon-nitrogen triple bond, an aromatic carbocyclic or heterocyclic system in β-position to the sulfonium center, unsaturated c-c bond, or c-heteroatom bond where the heteroatom is O, N, S.

In particular embodiments, a compound represented by formula (I) is disclosed:

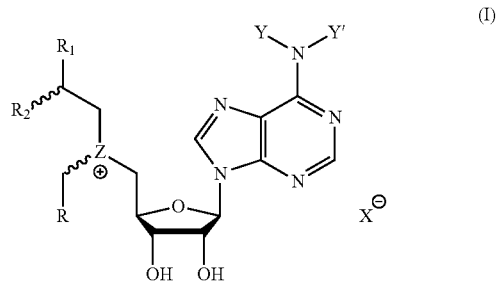

wherein

R1 is COOH or COO—

X is an organic or inorganic anion carrying one or more negative charges; and

R, R2, Y, and Y' are selected from the following:

| Y | Y' | R2 | R |
|---|---|---|---|
| H | H | BocNH- (tert-butyl carbamate) | phenyl |
| H | H | BocHN-CH< | vinyl (CH=CH$_2$) |
| H | H | BocHN-CH< | N$_3$-(CH$_2$)$_4$-CH=CH- |
| H | H | BocHN-CH< | N$_3$-(CH$_2$)$_3$-C≡C- |
| H | H | BocHN-CH< | H$_2$N-(CH$_2$)$_3$-C≡C- |
| H | H | BocHN-CH< | -CH(C(=O)OEt)- (ethyl ester) |
| H | H | H | phenyl |
| CH$_3$ | CH$_3$ | BocNH- (tert-butyl carbamate) | phenyl |
| H | H | H$_2$N-CH< | N$_3$-(CH$_2$)$_3$-C≡C- |

-continued
| Y | Y' | R2 | R |
|---|---|---|---|
| H | H |  | |
| H | H | 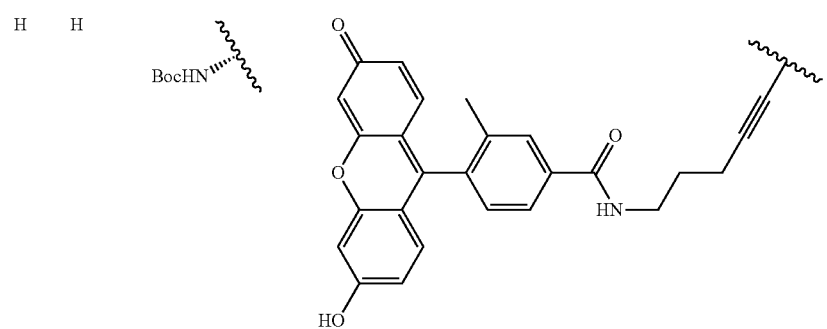 | |
| H | H | H | 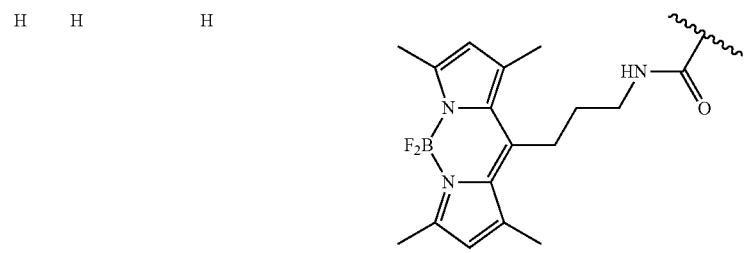 |
| H | H | NH2 | 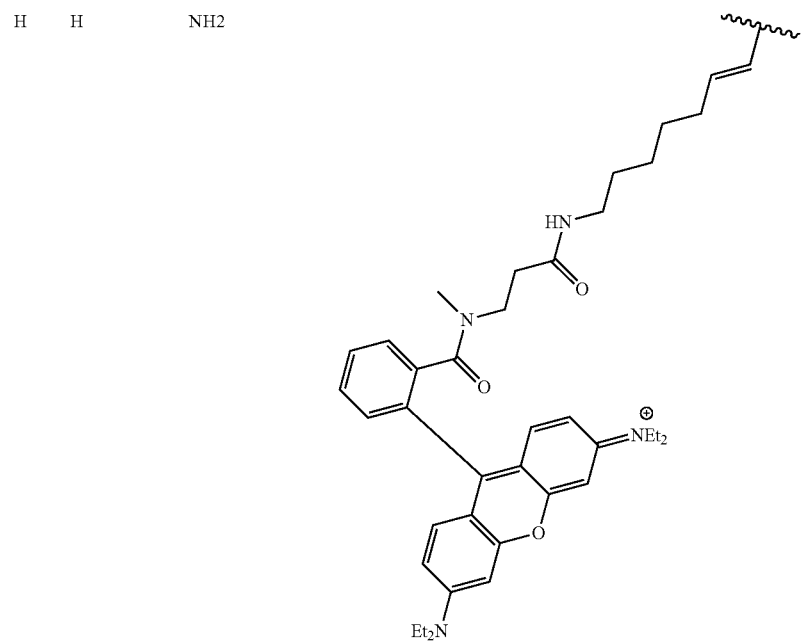 |

-continued
| Y | Y' | R2 | R |
|---|----|----|---|
| H | H | 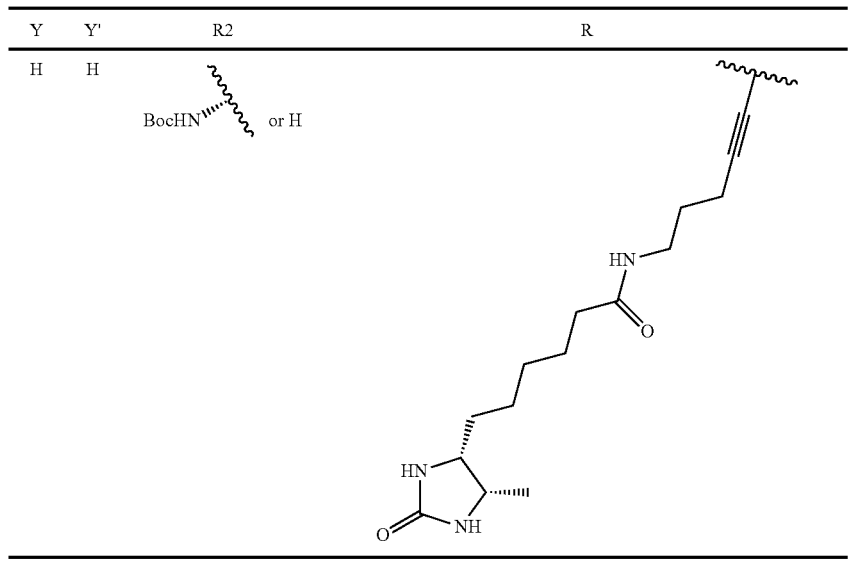 | |
In some embodiments, the compound is selected from the group comprising:
| Compound | Name |
|----------|------|
| 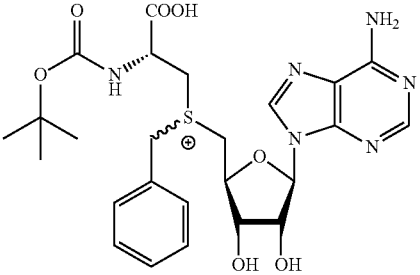 | (Benzyl)(5'-Deoxyadenosyl)-(N-Boc-L-Cysteine)sulfonium salt |
| 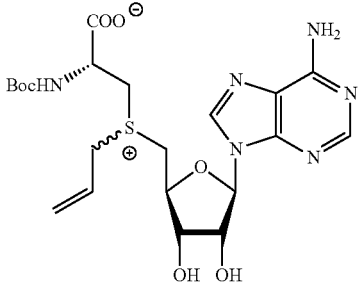 | (Allyl)(5'-Deoxyadenosyl)-(N-Boc-L-Cysteine)sulfonium salt |
| 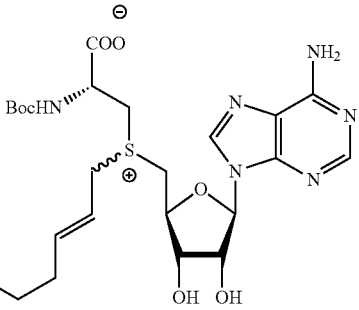 | (8-Azido-oct-2-ene)(5'-Deoxyadenosyl)-(N-Boc-L-Cysteine)sulfonium salt |

| Compound | Name |
|---|---|
| | (6-Azido-hex-2-yne)(5'-Deoxyadenosyl)-(N-Boc-L-Cysteine)sulfonium salt |
| | (6-Amino-hex-2-yne)(5'-Deoxyadenosyl)-(N-Boc-L-Cysteine)sulfonium salt |
| | (Ethyl Carboxymethyl)(5'-Deoxyadenosyl)-(N-Boc-L-Cysteine)sulfonium salt |
| | (Benzyl)(5'-Deoxyadenosyl)-(3-Propionate)sulfonium salt |
| | (Benzyl)(5'-Deoxy-$N^6$,$N^6$-dimethyladenosyl)-(N-Boc-L-Cysteine) sulfonium salt |

| Compound | Name |
|---|---|
| | (6-Azido-hex-2-yne)(5'-Deoxyadenosyl)-(L-Cysteine)sulfonium salt |
| | (6-Amino-hex-2-yne)(5'-Deoxyadenosyl)-(L-Cysteine)sulfonium salt |
| | Fluorescent sulfonium salt |
| | Fluorescent sulfonium salt II |

-continued

| Compound | Name |
|---|---|
| (structure) | Fluorescent sulfonium salt III |
| (structure) | Dethiobiotin sulfonium cofactor |

In an embodiment of the present invention said organic or inorganic anion is selected from trifluoroacetate, formate, halide and sulfonate.

In another preferred embodiment of the present invention, R additionally comprises at least one member selected from functional groups, heavy atoms or heavy atom clusters suitable for phasing of X-ray diffraction data, radioactive or stable rare isotopes, and a residue of a member selected from fluorophores, fluorescence quenchers, affinity tags, cross-linking agents, nucleic acid cleaving reagents, spin labels, chromophores, proteins, peptides or amino acids which may optionally be modified, nucleotides, nucleosides, nucleic acids which may optionally be modified, carbohydrates, lipids, transfection reagents, intercalating agents, nanoparticles and beads.

Preferred radioactive or stable rare isotopes are selected from the group consisting of 3H(T), 14C, 32P, 33P, 35S, 125I, 131I1 2H (D), 13Cl 15N, 17O and 18O. Furthermore, preferred stable isotopes are selected from the group consisting of 19F and 127I.

Preferred spin labels which are stable paramagnetic groups (typically a nitryl radical) are selected from the group consisting of 2,2,6,6,-tetramethyl-piperidin-1-oxyl and 2,2,5,5,-tetramethyl-pyrrolidin-1-oxyl.

Preferred amino acid modifications are selected from the group consisting of β- and γ-amino acids and preferred peptide modifications are selected from the group consisting of depsipeptides, vinylogous peptides, permethylated peptides, peptoids, azapeptides (azatides), oligocarbamates, oligoureas, oligosulfones, oligosulfonamides, oligosulfinamides, pyrrole-imidazole-hydroxypyrrole polyamides and peptide nucleic acids (PNA), more preferably said peptide modifications are pyrrole-imidazole-hydroxypyrrole polyamides and peptide nucleic acids (PNA).

Preferred nucleic acid modifications are selected from the group consisting of peptide nucleic acids (PNA), locked nucleic acids (LNA) and phosphorothioate modified nucleic acids.

Preferred transfection reagents are selected from the group consisting of cationic lipids (e.g. Lipofectamin and derivatives commercially available from Invitrogen, CA, USA), cationic polymers (e.g. polyethyleneimine (PEI) commercially available from Sigma) and polycationic dendrimers.

Preferred intercalating agents which are typically planar or near planar aromatic ring systems binding between neighbouring base-pairs in double-stranded nucleic acids are selected from the group consisting of ethidium, thiazole orange, acridine or a derivative thereof, and pyrene.

Preferred nanoparticles are selected from the group consisting of gold and silver clusters.

Preferred beads are selected from the group consisting of silica beads, magnetic beads and polystyrene microspheres (e.g. commercially available from Molecular Probes, OR, USA)

In one embodiment of the present invention, said functional group is selected from an amino group, a thiol group, a 1,2-diol group, a hydrazino group, a hydroxyamino group, a haloacetamide group, a maleimide group, an aldehyde group, a ketone group, an 1,2-aminothiol group, an azido group, an alkyne group, a 1,3-diene function, a dienophilic function (e.g. activated carbon-carbon double bond), an arylhalide group, a terminal alkyne group, an arylboronic acid group, a terminal haloalkyne group, a terminal silylalkyne group and a protected amino, thiol, 1,2-diol, hydrazino, hydroxyamino, aldehyde, ketone and 1,2-aminothiol group.

In another embodiment of the present invention, said fluorophore is selected from Alexa, BODIPY, bimane, coumarin, Cascade blue, dansyl, dapoxyl, fluorescein, mansyl, MANT, Oregon green, pyrene, rhodamine, Texas red, TNS, fluorescent nanocrystals (quantom dots), a cyanine fluorophore and derivatives thereof.

In another preferred embodiment of the present invention, said fluorescence quencher is selected from dabcyl, QSY and BHQ.

In yet another embodiment of the present invention, said affinity tag is selected from peptide tags, metal-chelating groups, isotope coded affinity tags, biotin, maltose, mannose, glucose, $N$-acetylglucosamine, $N$-acetylneuraminic acid, galactose, ^-acetylgalactosamine, digoxygenin and dinitrophenol.

In another embodiment of the present invention, said peptide tag is selected from his-tags, tags with metal chelating properties, strep-tags, flag-tags, c-myc-tags, HA-tags, epitopes and glutathione.

The term "affinity tag" as used herein relates inter alia to a label which can, for example, be used for affinity purification. A number of affinity tags which are in accordance with the present invention are well known in the art. Such tags may for example have metal chelating properties and may allow to bind the side chain —Z—R of cofactor (I) of the present invention, before or after methyltransferase-catalyzed transfer to a biomulecule, to a matrix used in Immobilized Metal Ion Affinity Chromatography (IMAC). The IMAC technique developed by Porath et al. (Porath et al., (1975) Nature 258, 598-599) is based on the interaction between certain protein superficial residues (histidines, cysteines, and in a lower degree tryptophans) and cations from transition metals which form chelates with polycarboxylic ligands. Typical conditions are described in the art and are known to the skilled person (Porath, (1992) Protein Expression and Purification 3, 263-281; Hemdan, and Porath, (1985) Journal of Chromatography 323, 255-264; Porath and Hansen, (1991) Journal of Chromatography 550, 751-764).

Other preferred tags include "strep-tag" which relates to an 8 amino acid streptavidin binding sequence. This sequence was found through the systematic screening of random peptide libraries in order to identify a peptide binding sequence with optimal affinity tag properties (Schmidt and Skerra, (1993) Prot. Engineering 6, 109-122). When attached to the side chain —Z—R of cofactor (I) of the present invention, modified nucleic acid molecules or (poly)peptides can be affinity purified, e.g. by using a gravity-flow column with a matrix containing StrepTactin, Streptavidin, Avidin or the like. Such matrices are commercially available from, e.g. Sigma-Genosys/The Woodlands (Tx, USA) or IBA/Goettingen (Germany).

Other preferred tags include the "flag-tag" which relates to an 8 amino acid peptide which binds to an anti-flag antibody. When attached to the side chain —Z—R of cofactor (I) of the present invention, modified nucleic acid molecules or (poly)peptides can be affinity purified, e.g. by using a gravity-flow column with a matrix containing an immobilized anti-flag antibody. Such matrix is commercially available from, e.g. Sigma-Aldrich.

Other preferred tags include "c-myc-tag" which relates to a 10 amino acid peptide which binds to an anti-c-myc antibody. When attached to the side chain —Z—R of cofactor (I) of the present invention, modified nucleic acid molecules or (poly)peptides can be affinity purified, e.g. by using a gravity-flow column with a matrix containing an immobilized anti-c-myc antibody. Such matrix is commercially available from, e.g. Pierce Biotechnology (IL, USA).

Other preferred tags include "HA-tag" which relates to 9 amino acid peptide which is derived from the surface hemagglutinin of influenza virus and binds to an anti-HA antibody. When attached to the side chain —Z—R of cofactor (I) of the present invention, modified nucleic acid molecules or (poly)peptides can be affinity purified, e.g. by using a gravity-flow column with a matrix containing immobilized anti-HA antibody.

In another embodiment of the present invention, said metal-chelating group is nitrilotriacetic acid, ethylenediaminetetraacetic acid (EDTA), 1,10-phenanthroline, a crown ether and a HiS4-8 peptide.

Preferably, said crosslinking agent is selected from mono- or bifunctional platinum(ll) complexes, maleimides, iodacetamides, aldehydes and photocrosslinking agents like arylazide, a diazo compound, a 2-nitrophenyl compound, psoralen and a benzophenone compound.

In another embodiment of the present invention, said heavy atom or heavy atom cluster is preferably selected from copper, zinc, selenium, bromine, iodine, ruthenium, palladium, cadmium, tungsten, platinum, gold, mercury, bismuth, samarium, europium, terbium, uranium, Ta6Br14, Fe4S4 and P2W-18O62 suitable for phasing X-ray diffraction data.

Preferred nucleic acid cleaving reagents are selected from the group consisting of iron-EDTA, copper-1,10-phenanthroline, acridine or a derivative thereof, an enediyne compound and a rhodium complex, more preferably said nucleic acid cleaving reagent is selected from iron-EDTA, copper-1,10-phenanthroline and a rhodium complex.

The present invention also relates to a complex of a compound (I) of the present invention and a methyltransferase which normally uses S-adenosyl-L-methionine (SAM or AdoMet) as a cofactor.

In a preferred embodiment of the present invention, said methyltransferase normally transfers the methyl residue of S-adenosyl-L-methionine (SAM or AdoMet) onto a nucleic acid molecule, a polypeptide, a carbohydrate or a small molecule. An overview on SAM (AdoMet)-dependent methyltransferases is for instance given by Kagan and Clarke, (1994) Archives of Biochemistry and Biophysics 310, 417-427. This article also gives a list of small molecule O-methyltransferases and small molecule N-methyltransferases which include for example catechol O-methyltransferase and glycine N-methyltransferase.

The terms "nucleic acid molecule", "polypeptide", "carbohydrate" or "small molecule" are sometimes referred to as biomolecules. Biomolecules may be entirely natural, i.e. unmodified, synthetic or modified and may exist as complexes. Accordingly, for example the term "nucleic acid molecule" comprises DNA and RNA molecules as well as modified DNA and RNA molecules. DNA may be for example cDNA or genomic DNA. RNA may be for example mRNA, hnRNA, spliced and unspliced RNA etc. Whenever the term polypeptide is used herein, it is to be understood as comprising protein, peptides and polypeptides. Peptides may be as short as for example 10, 11, 12, 13, 14, 15 or 16 residues in length.

In a more preferred embodiment of the present invention, said methyltransferase is an orphan DNA methyltransferase or part of a bacterial restriction modification system.

Said DNA methyltransferase may be selected from M.AacDam, M.AatlI, M.AbaORFDP, M.AbaORFKP, M.Abrl, M.Accl, M.Acclll, M.Acil, M.AclI, M.Acul, M.Afa22MI, M-AflIII M.Afllll, M.Agel, M.Ahdl, M.AhyBP, M.AIaK2l, M.AIul, M. AIwI, M.AIw26l, M.Apal, M.ApaLI, M.ApeKI, M.Apol, M.Aqul, M.Ascl, M.Asel, M.Asell, M-AsISI, M.AspCNI, M.AtuCI, M.AtuCORF1997P, M.AtuDORF794P, M.AtuDORF3839P, M.Aval, M.Avall, M.Avalll, M.AvaIVP, M.AvaV, M.AvaVI, M.AvaVII, M.AvaVIII, M.AvalX, M.AvaORF3700P, M.AvaORF7270P, M.Avrl, M.Avrll, M.Babl, M.Bael, M.Bali, M.BamHI, M.BamHII, M.Banl, M.Banll, M.Banlll, M.BatAORF3814P, M.BatA581ORF3846P, M.Bbu297l, M.Bbvl, MLBbvCI, M2.BbvCI, M.BbvSI, MLBccl, M2.Bccl, M.Bce1247l, MLBceAI, M2.BceAI, M.Bce14579ORF939P, M.BceSORF365P, M.BceSORF4605P, M1.BceSORF5606P, M2.BceSORF5606P, M.Bcepi P, M.Bcep43ORFAP, M.Bchl, M.Bcll, MLBcnl, M2.Bcnl (M.BcnlB), MLBcoKI, M2.BcoKI, M.Bcs139P, M.Bdil, M.Bepl, MLBfal, M2.Bfal, M.BfaORFC157P, M2.Bfil (M.BfiC2), MLBfuAI, M2.BfuAI, M.Bgll, M.Bgllll, MLBhal, M2.Bhal, M.Bhall, M.BjaORF2509P, M.BIoNORF564P, M.BIoNORF1473P, M.Blpl, M.Bmal, M.BmaPhiE125ORF56P, M.Bme216l, M.BmeLORF1444P, M.BmeTI, MLBmrl, M2.Bmrl, M.Bnal, M.Bpml, M1.Bpu10l, M2.Bpu10l, MLBsal, M2.Bsal, M.BsaAI, M.Bsall, M.BsaWI, MLBscGI, M2.BscGI, M.Bse634l, M.BseCI, M.BseDI, BseMII, BseRI, M.BseRI, M.BseYI, Bsgl, M.Bsgl, M.BsiWI, M.BsII, MLBsml, M2.Bsml, M.BsmAI, M.BsmBI, M.BsoBI, M.Bspl, M.Bspθl, M.BspδOI, M.Bsp98l, M.Bsp106l, M.Bsp143ll, BspCNI, M.BspCNI, M.BspEI, M.BspHI, M.BsplS4l, M.BspKTβl, BspLUH III, M1.BspLU11 lll, M2.BspLU11 IM, MLBspMI, M2.BspMI, M.BspMII, M.BspRI, M.BspSTδl, MlBsrl, M2.Bsrl, MLBsrBI, M2.BsrBI, M.BsrFI, M.BssHI, M.BssHIII, M.BssSI, M.Bstl, M.BstEII, M.BstEIII, M1.BstF5l, M2.BstF5l, M3.BstF5l, M4.BstF5l, M.BstGII, M.BstLVI, M.BstNI, M.BstNBI, M.BstVI, M.BstXI, M.BstYI, M.Bsu15l, M.Bsu36l, M.Bsu6633l, M.BsuBI, M.BsuEII, M.BsuFI, M.Bsu1330ORF491 P, M.BsuRI, M.BthlPS78, M.BthVORF4625P, M.BusLBORFC747P; M.BusLBORFC755P, M.Cacδl, M.Cac824l, M.Cac824ORF3358P, M.CauJORFC101P, M.CauJORFC102P, M.CauJORFC103P, M.CauJORFC104P, M.CauJORFC107P, M.CauJOR-FCHOP, M.CauJORFC111 P, M.Cbol, M.CcrMI, M.Cdi630l, M.CdiCDΘI, M.CdiCDβll, M.Cdi630ORFC898P, M.CefORF1493P, M.Ceql, M.Cfrl, M.Cfrθl, M.Cfrθl, M.Cfrl 0l, M.Cfrl 3l, M.Cfr42l, M.CfrAI, M.CfrBI, M.Cgll, M.CglASI, M.CglLPΘP, M.CjeNI, M.Cje81116ORFBP, M.Cje81116ORFCP, M.CIal, M.Cspβl, M.Csp68KI, M.Csp68KIV, M.Csp68KV, M.CteEORF387P, M.CthORFS26P, M.CthORFS34P, M.CthORFS93P, M.CviAI, M.CviAII, M.CviAIV, M.CviBI, M.CviBII, M.CviBIII, M.CviORF5P, M.CviORF2111 P, M.CviPI, M.CviQI, M.CviQII, M.CviQIII, M.CviQIVP, M.CviQVP, M.CviQVI, M.CviQVII, M.CviQVIIIP, M.CviQIVP, M.CviQXP, M.CviQXI, M.CviRI, M.CviRII, M.CviSI, M.CviSII, M.CviSIII, M.CviSIVP, M.CviSVP, M.CviSVIP, M.CviTI, M.Ddel, DhaORFC135P, MLDpnll, M2.Dpnll, M.Dral, M.Drall, M.Dralll, M.DsaV, M.DvuORF19P, M.DvuORF2842P, M.Eacl, M.Eael, M.Eagl, MLEarl, M2.Earl, M.Ecal, M.EcMδkl, M1.Eco31 l, M2.Eco31 l, M.Eco32l, M.Eco47ll, M.Eco47lll, M.Eco56l, Eco57l, M.Eco57l, M.Eco64l, M.Eco72l, M.Eco88l, M.Eco98l, M.Eco105l, M.Eco147l, M.Eco231 l, M.Eco255l, M.Eco536P, M.Eco1639P, M.Eco1831 l, M.Eco248534P, M.EcoAI, M.EcoBI, M.EcoCFTDamP, M.EcoCFTDam2P, M.EcoCFTDam3P, M.EcoCFTDcmP, M.EcoDI, M.EcoDR2, M.EcoDR3, M.EcoDXXI, M.Eco67Dam, M.EcoEI, M.EcoHI, M.EcoHK31 l, M.EcoKI, M.EcoKII, M.EcoKDam, M.EcoKDcm, M.EcoKO157DamP, M.EcoKO157Dam2P, M.EcoKO157Dam3P, M.EcoKO157DcmP, M.EcoKO157ORF1953P, M.EcoLahniP, M.EcoLahn3P, M.EcoNI, M.EcoNM2P, M.EcoO109l, M.EcoO157DamP, M.EcoO157DcmP, M.EcoO157ORF1454P, M.EcoO157ORF2389P, M.EcoO157ORF3349P, M.Eco536ORF3P, M.EcoPI, M.EcoP15l, M.EcoPIDam, M.EcoPhi4795DamP, M.EcoRI, M.EcoRII, M.EcoRV, M.EcoR124l, M.EcoR124lI, M.EcoRD2, M.EcoRD3, M.EcoStxi DamP, M.EcoStx2DamP, M.EcoT22l, M.EcoT38l, M.EcoTI Dam, M.EcoT2Dam, M.EcoT4Dam, M.EcoVIII, M.EcoVT2Dam, M.EcoWphiP, M.Eco29kl, M.EcopHSHP, M.EcopHSH2P, M.Ecoprrl, M.EfaHGSORFHP, M.EphP1ORF1 P, M.EsaBCl I, M.EsaBC3l, M.EsaBC4l, M.EsaBSl I, M.EsaBS9l, M.EsaDixi l, M.EsaDix2l, M.EsaDix3l, M.EsaDix4l, M.EsaDixδl, M.EsaDixθl, M.EsaDix7l, M.EsaLHCl, M.EsaLHCIII, M.EsaRMIP, M.EsaRM13P, M.EsaRM16P, M.EsaRM17P, M.EsaRM21 P, M.EsaRM38P, M.EsaRM61 P, M.EsaRM63P, M.EsaRM65P, M.EsaRM67P, M.EsaRM69P, M1EsaSI I, M2.EsaS1 l, M.EsaS3l, M.EsaS4l, M.EsaS6l, M.EsaS7l, M.EsaSδl, M.EsaSS2P, M.EsaSSδP, M.EsaSS12P, M.EsaSS13P, M.EsaSS15P, M.EsaSS16P, M.EsaSS18P, M.EsaSS19P, M.EsaSS22P, M.EsaSS30P, M.EsaSS31 P, M.EsaSS35P, M.EsaSS36P, M.EsaSS40P, M.EsaSS43P, M.EsaSS47P, M.EsaSS48P, M.EsaSS49P, M.EsaSS52P, M.EsaSS55P, M.EsaSS57P, M.EsaSS67P, M.EsaSS69P, M.EsaSS70P, M.EsaSS71P, M.EsaSS72P, M.EsaSS73P, M.EsaSS74P, M.EsaSS75P, M.EsaSS76P, M.EsaSS79P, M.EsaSS81P, M.EsaSS83P, M.EsaSS87P, M.EsaSS88P, M.EsaSS90P, M.EsaSS96P, M.EsaSS97P, M.EsaSS103P, M.EsaSS104P, M.EsaSS105P, M.EsaSS106P, M.EsaSS107P, M.EsaSS108P, M.EsaSS109P, M.EsaSSUOP, M.EsaSS111 P, M.EsaSS113P, M.EsaSS117P, M.EsaSS120P, M.EsaSS123P, M.EsaSS126P, M.EsaSS130P, M.EsaSS131 P, M.EsaSS134P, M.EsaSS136P, M.EsaSS137P, M.EsaSS144P, M.EsaSS145P, M.EsaSS150P, M.EsaSS153P, M.EsaSS154P, M.EsaSS155P, M.EsaSS156P, M.EsaSS160P, M.EsaSS163P, M.EsaSS165P, M.EsaSS167P, M.EsaSS169P, M.EsaSS170P, M.EsaSS172P, M.EsaSS174P, M.EsaSS177P, M.EsaSS181 P, M.EsaSS182P, M.EsaSS186P, M.EsaSS187P, M.EsaSS192P, M.EsaSS195P, M.EsaSS200P, M.EsaSS214P, M.EsaSS215P, M.EsaSS216P, M.EsaSS218P, M.EsaSS221 P, M.EsaSS222P, M.EsaSS223P, M.EsaSS225P, M.EsaSS228P, M.EsaSS237P, M.EsaSS238P, M.EsaSS241 P, M.EsaSS244P, M.EsaSS245P, M.EsaSS246P, M.EsaSS247P, M.EsaSS254P, M.EsaSS259P, M.EsaSS264P, M.EsaSS266P, M.EsaSS268P, M.EsaSS269P, M.EsaSS270P, M.EsaSS275P, M.EsaSS278P, M.EsaSS281 P, M.EsaSS282P, M.EsaSS283P, M.EsaSS289P, M.EsaSS297P, M.EsaSS302P, M.EsaSS303P, M.EsaSS305P, M.EsaSS315P, M.EsaSS317P, M.EsaSS318P, M.EsaSS319P, M.EsaSS323P, M.EsaSS326P, M.EsaSS328P, M.EsaSS329P, M.EsaSS334P, M.EsaSS335P, M.EsaSS336P, M.EsaSS51 DamP, M.EsaSS65DamP, M.EsaSS138DamP, M.EsaSS198DamP, M.Esp3I, M.Esp1396I, M.EspRB49DamP, M.FauI, M.FnuDI, M.FnuDII, M.FnuDIII, M.Fnu4HI, M.FnuVDamP, M.FokI, M.FseI, M.FspI, M.FssI, M.GmeORFCΘP, M.GmeORFC16P, M.GsuI, M.GviDamP, M.H2I, M.HaeII, M.HaeIII, M.HapII, M.HduDamP, MLHgaI, M2.HgaI, M.HgiAI, M.HgiBI, M.HgiCI, M.HgiCII, M.HgiDI, M.HgiDII, M.HgiEI, M.HgiGI, M.HhaI, M.HhaII, M.HheORF238P, M.HheORF1050P, M.HheORF1244P, M.HheORF1445P, M.HinIII, M.HinB23lORFDP, M.HinHPI Dam, M.HinHP2Dam, M.HinPII, M.HincII, M.HindI, M. HindII, M.HindIII, M.HindV, M.HindDam, M.HinfI, M.HinfIII, M.HjaI, M.HpaI, M.HpaII, MLHphI, M2.HphI, M.HpyI, M.Hpyδl, M.Hpy87AP, M.Hpy99I, M.Hpy99II, M.Hpy99III, M.Hpy99IV, M1.Hpy99V, M2.Hpy99VP, M.Hpy99VI, M.Hpy99VIII, M.Hpy99IX, M.Hpy99X, M.Hpy99XI, M.Hpyl66IV, M.Hpyl78IP1 M.Hpy188I, M.Hpy188II, M.Hpy188III, M.Hpy788606P, M.Hpy788845P, M.Hpy788849P, M.Hpy789115P, M.Hpy789117P, M.Hpy789137P, M.Hpy789145P, M.Hpy790101P, M.Hpy959772P, M.HpyAI, MLHpyAII, M2.HpyAII, M.HpyAIII, M.HpyAIV, M.HpyAV, MLHpyAVI, M2.HpyAVI, M.HpyAVII, M.HpyAVIII, M.HpyAIX, M.HpyAX, M.Hpy87AI, M.HpyAORF263P, M.HpyAORF369P, M.HpyAORF481P, M.HpyAORF483P, M1.HpyC1 1, M2.HpyC1 1, M.HpyCH4IV, M.HpyCH4V, M.HpyCR2ORF1P, M.HpyCR2ORF3P, M1.HpyCR4RM1 P, M2.HpyCR4RM1 P, M.HpyCR9RM1 P, M.HpyCR9RM2P, M.HpyCR14RM1 P, M.HpyCR14RM2P, M.HpyCR15RM2P, M.HpyCR16RM1P, M.HpyCR29RM1 P, M.HpyCR29RM2P, M.HpyCR35RM1 P, M.HpyCR35RM2P, M1.HpyCR38RM1 P, M2.HpyCR38RM1 P, M.HpyCR38RM2P, M.HpyF17l,
M.Hpy99ORF430P, M.Hpy99ORF433P, M.Hpy99ORF846P, M.Hpy99ORF1012P, M.HspNORF1543P, M.KasI, M.KpnI, M.Kpn2I, M.KpnAI, M.KpnBI, M.Kpn19097DamP, M.Kpn19097Dam2P, M.Kpn19097ORFFP, M.Kpn2kl, M.Lci22RP, M.LinFORF11323P, M.LinFORF12222P, M.LinFORF12737P, M.Linl_ORF903P, M.LinLORF1547P, M.LinLORF2668P, MLLIaAI, M2.LlaAI, M. LIaBI, M.LIaCI, M.LIaDI, M.LIaDII, MLLIaDCHI, M2. LIaDCHI, M.LIaKR2l, M.LmoAP, M.LmoEORF470P, M.LmoFORF327P, M.Lmo19115ORF1 P, M.Lsp1109l, M.MamI, MLMboI, M2.MboI, MLMboII, M2.MboII, M.Mca43617ORFAP, M.Mca43617ORFBP, M1.Mca43617ORFDP, M2.Mca43617ORFDP, M.Mca43617ORFJP, M.MfeI, M.MjaI, M.MjaII, M.MjaIII, M.MjaIVP, M.MjaV, M.MjaVI, M.MIoORFmlr7520P, M.MluI, M.MlyI, M.MmaMORFC174P, M.MmaSORF735P, M.MmeI, M.MmeII, M.MmoORF950P, M.MmoORF3450P, M.MmyIP, M.MmySCORF186P, M.MmySCORF216P, M.MmySCORF950P, MLMnlI, M2.MnlI, M.MpeORF1230P, M1.MpeORF1780P, M2.MpeORF1780P, M.MpeORF4940P, M.MpeORF9800P, M.MpuCORF430P, M.MscI, M.MseI, M.MsmChe9cORF76P, M.MsmChe9cORF77P, M.MsmChe9cORF80P, M.MsmcdP, M.MsmomegaORF127P, M.MspI, M.MspAI I, M.MspSDIOI, M.MthFI, M.MthTI, M.MthZI, M.MunI, M.MvaI, M.Mva1269l, M.MwoI, M.NaeI, M.NarAORFC306P, M.NcoI, M.NdeI, M.NdeII, M.Ngo18785P, M.Ngo185840P, M.Ngo185841 P, M.NgoAI, M.NgoAII, M.NgoAIII, M.NgoAIV, M.NgoAV, M.NgoAVIIP, M.NgoAXIP, M.NgoAORFC708P, M1.NgoAORFC717P, M2.NgoAORFC717P, M.NgoBI, M.NgoBII, M.NgoBIIIP, M.NgoBIVP, M.NgoBV, MLNgoBVIII, M2.NgoBVIII, M.NgoBIX, M.NgoBXII, M.NgoDIII, M.NgoEI, M.NgoFVII, M.NgoGI, M.NgoGII, M.NgoGIII, M.NgoGIVP, M.NgoGV, M.NgoHIP, M.NgoHIIP, M.NgoHIIIP, M.NgoHIVP, M.NgoHVP, M.NgoHVIP; M.NgoHVIIP, M.NgoHVIII, M.NgoKVIP, M.NgoLIP, M.NgoLII, M.NgoLIIIP, M.NgoLIVP, M.NgoLVP, M.NgoMI, M.NgoMII, M.NgoMIII, M.NgoMIV, M.NgoMV, M.NgoMVIII, M.NgoMXV, M.NgoNIP, M.NgoNII, M.NgoNIIIP, M.NgoNIVP, M.NgoNVP, M.NgoPIP, M.NgoPII, M.NgoPIII, M.NgoPIVP, M.NgoPVP, M.NgoQIP, M.NgoQIIP, M.NgoQIIIP, M.NgoQIVP, M.NgoQVP, M.NgoSIP, M.NgoSII, M.NgoSIIIP, M.NgoSIVP, M.NgoSVP, M.NgoTIP, M.NgoTII, M.NgoTIIIP, M.NgoTIVP, M.NgoTVP, M.Ngo125VIIP, M.NlaI, M.NlaIII, M.NlaIV, M.NlaX, M.NlaL17ORFAP, M.NmaPhiChi 1, M.NmeAORF1453P, M.NmeAORF1500P, MLNmeBI, M2.NmeBI, M.NmeBF13P, M.NmeBORF1033P, M.NmeBORF1290P, M.NmeSI, M.NmeST1117ORF1 P, M.NmepNLEI P, M.NpuORFC221 P, M.NpuORFC222P, M.NpuORFC224P, M.NpuORFC226P, M.NpuORFC228P, M.NpuORFC230P, M.NpuORFC231 P, M.NpuORFC234P, M.NsiI, M.NspI, M.NspIII, M.NspV, M.NspHI, M.OihORF3333P, M.OihORF3336P, M.OkrAI, M.Pac25l, M.PaeI, M.Pae1MORF3201 P, M.PaeMSHORFI P, M.Pae2164ORF7P, M.PaeR7l, M.PfIMI, M.PgiI, M.PhaI, M.PhiBssHII, M.PhiMxδl, M.Phi3TI, M.Phi3TII, M.PhoI, M.PhoII, M.PhoWORFBP, M.PhsOYDamI P, M.PhsOYDam2P, M.PhsOYDam3P, M.PhsOYDam4P, M.PhsOYDamδP, M.PIeI, M.PIeLFBORFδP, M.PIuTDamP, M.PIuTDcmP, M.PIuTORF600P, M.PIuTORF2710P, M.PIuTORF2942P, M.Pmi16525DamP, M.Pmi16525Dam2P, M.Pmi16525ORFDP, M.PmuADam, M.PmuDam, M.Ppu21 1, M.PpuH H, M.Ppu1253l, M.PpuMI, M.PshAI, M.PspGI, M.PspPI, M.PstI, M.PvuI, M.PvuII, M.PvuRtsI DamP, M.PvuRtsI Dam2P, M.RcoORF690P, M.ReuORF325P, M.RhoIIsI, M.RhoUsII, M.RIe39BI, M.RmeADam, M.RpaORF1026P, M.RpapRPA4P, M.Rrh4273I, M.RruMORF SSP, M.RruMORFS15P, M.RsaI, M.RshI, M.RshIII, M.RsrI, M.RsrII, M.SPBetaI, M.SPRI, M.SacI, M.SacII, M.SalI, M2.SapI, M.Sau96I, M.Sau3239I, M.Sau6782I, M.Sau3AI, M.SauLPI, M.SbaI, M.SbfI, M.Sbo13I, M.ScaI, MLScrFI, M2.ScrFI, M.SduI, M.SenPI, M.SenPhiE15P, M.SenPhiE15DamP, M.SenpCI, M.SeqORFC57P, M.SeqORFC272P, M.SeqORFC448P, M.SfaNI, M.SfeI, M.SfiI, M.Sfl2DamP, M.Sfl2DcmP, M.Sfl2ORF3300P, M.SflSf6DamP, M.SflTDamP, M.Sf IT Dcm P, M.SflTORF3517P, M.Sfl2aI, M.SfoI, M.Sho27844P, M.SinI, M.SmaI, M.SmaII, M.SmapR478DcmP, M.SmapR478ORF272P, M.SmeIP, M1.SmuUORF504P, M2.SmuUORF504P, M.SnaBI, M.SonDamP, M.SonORF4P, M.SpeI, M.SphI, M.Spn526P, M.SpnθBI, M1.Spn19FORF24P, M2.Spn19FORF24P, M.Spn19FORF927P, M.SpnHGORF4P, M.SpnORF1431 P, M.SpnORF1849P, M.SpnRORF1287P, M.SpomI, M.SptAI, M.SscLH, M.Sse9I, M.SsMI, M.SsoI, M.SsoII, M.Ssp6803I, M.Ssp6803ORF729P, M.Ssp6803ORF1803P, M.SspPhiBti P, M.SssI, M.SstI, M.Ssu211I, M.Ssu212I, M1.Ssu2479I, M2.Ssu2479I, M1.Ssu4109I, M2.Ssu4109I, M1.Ssu4961I, M2.Ssu4961I, M1.Ssu8074I, M2.Ssu8074I, M1.Ssu11318I, M2.Ssu11318I, M1.SsuDAT1I, M2.SsuDAT1I, M.Sth368I, M.SthStβ1P, M.StsI, M.StyI, M.StyCDamP, M.StyCDam2P, M.StyCDam3P, M.StyCDam4P, M.StyCDcmP, M.StyD4I, M.StyDam, M.StyDam2P, M.StyDam3P, M.StyI 344Dam, M.Sty14028Dam, M.StyHCM1ORF187P, M.StyLTI, M.StyLTIII, M.StyI_T2Dam, M.StyLT2DcmP, M.StyLT2FelsDamP, M.StyR27ORF154P, M.StySJI, M.StySKI, M.StySPI, M.StySQI, M.StySopEDamP, M.StyTDamP, M.StyTDam2P, M.StyTDam3P, M.StyTDam4P, M.StyTDcmP, M.SuaI, M.TaeII, M.TaqI, M.TdeII, M.TdeIII, M.TdeORF706P, MTeIBORFI 578P, M.TelBORF1640P, MTeIBORFI 878P, M1 TerORFS1 P, M2TerORFS1 P, MTerORFS14P, MTerORFS18P, M.TerORFS62P, MTerORFS122P, MTfiTok6A11, M.ThaI, MThaII, MThaIII, MTIiI, M.TmaI, M.TpaI, M.TrsKTI, MTrsSI, M.TrsTI, MTseI, MTsp32I, MTsp45I, M.Tsp509I, M.TspRI, MTtM 111, TthU HI, M.TthHBβ1, M.TthHB27P, M.TthHB27ORF41 P, M.TvoORF849P, M.TvoORF1192P, M.TvoORF1400P, M.TvoORF1413P, M.TvoORF1416P, M.TwhORF771 P, M.TwhTORF783P, M.Uba580P, M.Ucri P, M.Van91 lI, M.VchADamP, M.Vch569BdamP, M.VchO395Dam, M.VchK139I, M.VpaRDamP, M.VspI, M.VvuDamP, M.VvuYDamP, M.WsuORF1405P, M.WsuORF1930P, M.XamI, M.XaxCORF2436P, M.XbaI, M.XcmI, M.XcyI, M.XfaAORFC345P, M.XfaAORFC348P, M.XfaOORFC725P, M.XfaORF1804P, M.XfaTORF577P, M.XfaTORF1062P, M.XfaTORF1607P, M.XhoI, M.XhoI, M.XmaI, M.XmaIII, M.XmnI, M.XorII, M.XphI, M.YenI, M.YenSDamP, M.YenSORFC666P, M.YenWI, M.YpeDamP, M.YpeKDamP, M.YpeKORF2224P, M.YpeKORF3792P, M.YpeMDamP, M.YpeMORF1932P, M.YpeMORF3790P, M.YpeORF391 P, M.YpeORF2088P, M.YpsDam.

In a more preferred embodiment of the present invention, the methyltransferase is selected from the group consisting of the DNA methyltransferases M.TaqI, M.HhaI, M.XbahI, M.PvuII, M.BsahI, M.FokI, M.BcnIB (M2.Bcnl), M.SssI, M.MpeI, M.PstI, M.XhoI, M.BseCI, M. M.RsrI, M.EcoRI, or a derivative thereof.

The present invention also relates to a kit comprising a compound (I) of the present invention. The various components of the kit may be packed in one or more containers, optionally dissolved in suitable buffer for storage. A leaflet with instructions for use may be added.

In a preferred embodiment of the present invention, the kit of the present invention further comprises a methyltransferase as defined in the present invention.

The present invention also relates to a kit comprising a complex of the present invention.

The present invention also relates to a pharmaceutical composition comprising a compound (I) of the present invention or a complex of the present invention and optionally a pharmaceutically acceptable carrier.

The present invention also relates to a diagnostic composition comprising a compound (I) of the present invention or a complex of the present invention. According to one embodiment, the diagnostic composition is a liquid composition. The preferred solvent of the diagnostic composition is aqueous in nature. In addition, the composition may contain other ingredients or carriers for modifying or maintaining the pH, osmolarity, viscosity, clarity, color, sterility, stability, rate of dissolution, or odor of the formulation. Similarly, the composition may contain still other pharmacologically acceptable ingredients for modifying or maintaining the stability, rate of dissolution, release, or absorption of the diagnostic composition. Once the diagnostic composition has been formulated, it may be stored in sterile vials as a solution, suspension, gel, emulsion, solid, or dehydrated or lyophilized powder. Such formulations may be stored either in ready to use form or requiring reconstitution immediately prior to use.

The present invention also relates to the use of a compound (I) of the present invention or a mixture thereof for modifying a target molecule. Typical uses are methods according to the teaching of the present invention such as the methods described herein.

In a preferred embodiment of the present invention, the modification of the target molecule is achieved by using a compound (I) of the present invention or mixtures thereof as a cofactor of a methyltransferase which transfers part of the compounds onto the target molecule.

In a preferred embodiment of the present invention, the target molecule is a nucleic acid molecule, a polypeptide optionally modified in a sequence-specific manner, a carbohydrate or a small molecule.

In a preferred embodiment of the present invention, the nucleic acid molecule is DNA, RNA or a hybrid thereof, more preferably the DNA or RNA molecule is modified in a sequence-specific manner.

In another more preferred embodiment of the present invention, the small molecule is selected from phospholipids, amino acids, hormones, nucleotides, nucleosides and derivatives thereof.

In another more preferred embodiment of the present invention, the methyltransferase is a DNA methyltransferase as defined above.

The present invention also relates to a method for the preparation of a modified target molecule comprising the incubation of the target molecule with a compound (I) of the present invention in the presence of a methyltransferase which is capable of using the compound as a cofactor and under conditions which allow for the transfer of part of the compounds onto the target molecule.

In a preferred embodiment of the present invention, the target molecule is a nucleic acid molecule, a polypeptide, a carbohydrate, or a small molecule or a complex between them.

In a more preferred embodiment of the present invention, the small molecule is a phospholipid, an amino acid, a hormone, a nucleotide, a nucleoside or a derivative thereof.

In a more preferred embodiment of the present invention, the polypeptide is modified in a sequence-specific manner.

In a more preferred embodiment of the present invention, the DNA or RNA molecule is modified in a sequence-specific manner.

In another more preferred embodiment of the present invention, the modification results from the transfer of a group onto the target molecule which is suitable as a label and which allows for the identification of the labeled molecule among other unlabeled molecules. Finally, in a more preferred embodiment of the present invention, the label is selected from fluorophores, fluorescence quenchers, affinity tags, spin labels, mass tags, radioactive or stable rare isotopes, chromophors and a detectable nanoparticle.

The present invention also relates to a method for detecting sequence-specific methylation in a biomolecule, comprising: (a) contacting a biomolecule with an S-adenosyl-L-methionine-dependent methyltransferase in the presence of a detectable cofactor of said methyltransferase; and (b) detecting whether the recognition site of said methyltransferase has been modified with the cofactor or a derivative thereof, wherein modification of the recognition site of said methyltransferase is indicative of an absence of methylation at said recognition site, wherein said cofactor is the compound of formula (I) of the present invention or a derivative thereof, which is described herein above in detail.

The term "biomolecule" means DNA, RNA or (poly) peptide. The term "(poly)peptide" refers alternatively to peptide or to polypeptide. Peptides conventionally are covalently linked amino acids of up to 30 residues, whereas polypeptides (also referred to as "proteins") comprise 31 and more amino acid residues. Preferably, the biomolecule is chromosomal or genomic DNA.

The term "contacting a biomolecule with a methyltransferase" means bringing into contact the biomolecule with the methyltransferase. Generally, this may be done by adding the methyltransferase to a sample containing the biomolecule. Alternatively, the sample containing the biomolecule may be added to a solution containing the methyltransferase. The skilled person knows that particular buffer conditions might be required for optimal enzyme activity. These conditions are either known to the skilled person or can be obtained by studying enzyme activity under various assay conditions.

Normally, the biomolecule is contacted by the methyltransferase in the presence of a cofactor of the methyltransferase. Preferably, said cofactor is the compound of formula (I) or a derivative thereof, which is described herein above in detail.

The term "methyltransferase" refers to enzymes normally transferring the activated methyl from S-adenosyl-L-methionine (AdoMet) onto their substrate. Preferably, the methyltransferase is an enzyme capable of methylating DNA, RNA or (poly)peptides. More preferably, the methyltransferase is a DNA methyltransferase selected from M.TaqI, M.HhaI, M.XbahI, M.PvuII, M.BsahI, M.FokI, M.BcnlB (M2.Bcnl), M.SssI, M.MpeI, M.PstI, M.XhoI, M.BseCI, M.Rsrl, M.EcoRI or a derivative thereof.

The term "detecting whether the recognition sequence of said methyltransferase has been modified with the cofactor or a derivative thereof means assessing whether the cofactor of formula (I) or a derivative thereof is attached to the biomolecule. Preferably, detection methods involve identifying the particular residue, within the recognition sequence of the methyltransferase, modified by the cofactor or the derivative thereof. Said derivative may be any compound resulting from the reaction between the compound of formula (I) or a derivative thereof and the biomolecule.

The term "recognition sequence" refers to the particular sequence within the biomolecule recognized by the methyltransferase. In case the methyltransferase is a DNA methyltransferase, the recognition sequence may comprise 2, 3, 4, 5, 6, or 8 nucleotides or nucleotide pairs. As used herein, the recognition sequence normally comprises the acceptor site for the compound of formula (I) of the present invention or the derivative thereof. The teaching of the present invention allows sequence-specific labeling in a methylation-dependent manner. DNA labeling of cytosine residues located in so-called CpG islands is a particular aspect of the present invention, as this allows to assess the methylation status of human chromosomal DNA. Therefore, the methods of the present invention are particularly useful for, but not limited to, diagnosing diseases associated with an altered methylation status of the chromosomal DNA. It should also be useful to access the methylation status of DNA from other sources as well as the methylation status of RNA or (poly) peptides. In addition, the cofactor of formula (I) or a derivative thereof in complex with a methyltransferase could be used to sequence-specifically label DNA, RNA or (poly) peptides which should be useful for various applications in biochemistry, molecular biology, gene therapy and nanobiotechnology. Furthermore, the cofactor of formula (I) or a derivative thereof could be used to find new methylation targets for methyltransferases.

In a preferred embodiment of the present invention, said biomolecule is a nucleic acid molecule or a (poly)peptide. Nucleic acid molecules shall be understood to encompass DNA and RNA. Preferably, DNA is chromosomal or genomic DNA. The biomolecule may be of any length. The term "chromosomal DNA" also encompasses fragments of a chromosome. Preferably, said fragment has a length of up to 500 nucleotides (nt), 1 kilobase (kb), 2 kb, 3 kb, 4 kb, 5 kb, 6 kb, 7 kb, 8 kb, 9 kb, 10 kb or even longer. However, also encompassed by the term chromosomal DNA are short fragments with a length of up to 5 nt, 10 nt, 15 nt, 20 nt, 25 nt, 30 nt, 35 nt, 40 nt, 45 nt, 50 nt, 100 nt, 200 nt, 300 nt, 400 nt, 500 nt.

In yet another preferred embodiment of the present invention, said step (a) is performed in vitro, with cell extracts or in vivo. Generally, suitable reaction conditions for treatment with restriction enzymes and DNA methyltransferases are known to the skilled person and are documented, for example, in standard textbooks of molecular biology (see e.g. Sambrook et at., "Molecular Cloning, A Laboratory Manual"; ISBN: 0879695765, CSH Press, Cold Spring Harbor, 2001). Suitable conditions for cofactor labeling mediated by M.SssI variant Q142A are, e.g. 300 µM of the compound of formula (I) or a derivative thereof, 31.3 fmol double-stranded DNA, 73 pmol M.SssI variant Q142A in buffer (10 mM Tris hydrochloride, 50 mM sodium chloride, 1 mM dithiothreitol, pH 7.9). Incubation may be performed at 37° C. for 4 h. When the methods of the present invention are carried in vitro a biological sample is isolated from an individual prior to analysis. The term "biological sample" relates to the specimen taken from the individual. Preferably, said specimen is taken from hair, skin, mucosal surfaces, body fluids, including blood, plasma, serum, urine, saliva, sputum, tears, liquor cerebrospinalis, semen, synovial fluid, amniotic fluid, breast milk, lymph, pulmonary sputum, bronchial secretion or stool.

The individual may be a human or an animal. Preferably, the individual is avian including turkey or hen, or the individual is a mammal including human, primate, rat, mouse, guinea pig, pig, cattle, cat or rabbit.

In a more preferred embodiment of the present invention, said nucleic acid molecule is DNA. Preferably, said DNA is chromosomal DNA.

In another more preferred embodiment of the present invention, the method further comprises prior to step (a) a step of treating the DNA with a restriction enzyme. Restriction enzymes may be selected from the group consisting of R.Aatll, R.Accl, R.Acc65l, R.Acil, R.Acll, R.Afel, R.Aflll, R.Afllll, R.Agel, R.Ahdl, R.AIul, R.AIwl, R.AIwNI, R.Apal, R.ApaLI, R.Apol, R.Ascl, R.Asel, R.AsiSI, R.Aval, R.Avall, R.Avrll, R.Bael, R.BamHI, R.Banl, R.Banll, R.Bbsl, R.Bbvl, R.BbvCI, R.BceAI, R.Bcgl, R.BciVI, R.Bcll, R.Bfal, R.BfrBI, R.BfuAI, R.Bgll, R.Bglll, R.BIpl, R.Bme1580l, R.BmgBI, R.Bmrl, R.Bpml, R.Bsal, R.BsaAI, R.BsaBI, R.BsaHI, R.BsaJI, R.BsaWI, R.BsaXI, R.BseRI, R.Bsgl, R.BsiEI, R.BsiHKAI, R.BsiWI, R.Bsll, R.Bsml, R.BsmAI, R.BsmBI, R.BsmFI, R.BsoBI, R.Bsp1286l, R.BspCNI, R.BspDI, R.BspEI, R.BspHI, R.BspMI, R.Bsrl, R.BsrBI, R.BsrDI, R.BsrFI, R.BsrGI, R.BssHII, R.BssKI, R.BssSI, R.BstAPI, R.BstBI, R.BstEII, R.BstFδl, R.BstNI, R.BstUI, R.BstXI, R.BstYI, R.BstZ17l, R.Bsu36l, R.Btgl, R.Btrl, R.Btsl, R.Cacδl, R.CIal, R.Ddel, R.Dpnl, R.Dpnll, R.Dral, R.Dralll, R.Drdl, R.Eael, R.Eagl, R.Earl, R.Ecil, R.EcoNI, R.EcoO109l, R.EcoRI, R.EcoRV, R.Faul, R.Fnu4HI, R.Fokl, R.Fsel, R.Fspl, R.Haell, R.Haelll, R.Hgal, R.Hhal, R.HinPI I, R.Hincll, R.Hindlll, R.Hinfl, R.Hpal, R.Hpall, R.Hphl, R.Hpy99l, R.Hpy188l, R.Hpy188lll, R.HpyCH4lll, R.HpyCH4IV, R.HpyCH4V, R.Kasl, R.Kpnl, R.Mbol, R.Mboll, R.Mfel, R.MIul, R.MIyl, R.Mnll, R.Mscl, R.Msel, R.Msll, R.Mspl, R.MspAI I, R.Mwol, R.Nael, R.Narl, R.Ncil, R.Ncol, R.Ndel, R.NgoMIV, R.Nhel, R.NIalll, R.NIalV, R.Notl, R.Nrul, R.Nsil, R.Nspl, R.Pacl, R.PaeR7l, R.Pcil, R.PflFI, R.PflMI, R.PIel, R.Pmel, R.Pmll, R.PpuMI, R.PshAI, R.Psil, R.PspGI, R.PspOMI, R.Pstl, R.Pvul, R.Pvull, R.Rsal, R.Rsrll, R.Sacl, R.Sacll, R.Sall, R.Sapl, R.Sau96l, R.Sau3AI, R.Sbfl, R.S cal, R.ScrFI, R.SexAI, R.SfaNI, R.Sfcl, R.Sfil, R.Sfol, R.SgrAI, R.Smal, R.Smll, R.SnaBI, R.Spel, R.Sphl, R.S spl, R.Stul, R.Styl, R.Swal, R.Taql, R.Tfil, R.Tlil, R.Tsel, R.Tsp45l, R.Tsp509l, R.TspRI, R.TthH H, R.Xbal, R.Xcml, R.Xhol, R.Xmal and R.Xmnl.

In yet another more preferred embodiment of the present invention, said DNA molecule is immobilized on a solid support. Solid supports that may be employed in accordance with the invention include filter material, chips, wafers, microtiter plates. Immobilization on the solid support may be achieved by different means including covalent coupling to an activated surface or by hybridization to nucleic acid molecules.

In another more preferred embodiment of the present invention said DNA molecule is coupled to the solid support by hybridizing the DNA molecule to an oligonucleotide which is attached to said solid support. Hybridization conditions may be of low, intermediate or high stringency. The term "stringent conditions", as used herein, is well known to the skilled artesian and corresponds to conditions of high stringency. Appropriate stringent hybridization conditions for each sequence may be established by a person skilled in the art by modifying parameters such as temperature, composition of the nucleic acid molecules, salt conditions etc.; see, for example, Sambrook et al., "Molecular Cloning, A Laboratory Manual"; ISBN: 0879695765, CSH Press, Cold Spring Harbor, 2001 or Higgins and Hames (eds.), "Nucleic acid hybridization, a practical approach", IRL Press, Oxford 1985, see in particular the chapter "Hybridization Strategy" by Britten & Davidson, 3 to 15. Stringent hybridization conditions are, for example, conditions comprising overnight incubation at 42° C. in a solution comprising: 50% formamide, 5×SSC (750 mM NaCI, 75 mM trisodium citrate), 50 mM sodium phosphate (pH 7.6), 5×Denhardt's solution, 10% dextran sulfate, and 20 µg/mL denatured, sheared salmon sperm DNA, followed by washing the filters in 0.1×SSC at about 650 C. Other stringent hybridization conditions are for example 0.2×SSC (30 mM NaCI, 3 mM sodium citrate, pH 7) at 65° C. In addition, to achieve even lower stringency, washes performed following stringent hybridization can be done at higher salt concentrations (e.g. 5×SSC). Note that variations in the above conditions may be accomplished through the inclusion and/or substitution of alternate blocking reagents used to suppress background in hybridization experiments. Typical blocking reagents include, but are not limited to, Denhardt's reagent, BLOTTO, heparin, denatured salmon sperm DNA, and commercially available proprietary formulations. The inclusion of specific blocking reagents may require modification of the hybridization conditions described above, due to problems with compatibility. Also contemplated are hybridization conditions of lower stringency.

Changes in the stringency of hybridization and signal detection are, for example, accomplished through the manipulation of formamide concentration (lower percentages of formamide result in lowered stringency), salt conditions, or temperature. For example, lower stringency conditions include an overnight incubation at 370 C in a solution comprising 6×SSPE (20×SSPE=3 M NaCI, 0.2 M NaH2PO4, 0.02 M EDTA, pH 7.4), 0.5% SDS1 30% formamide, 100 µg/mL salmon sperm blocking DNA; followed by washes at 50° C. with 1×SSPE, 0.1% SDS. In addition, to achieve even lower stringency, washes performed following stringent hybridization can be done at higher salt concentrations (e.g. 5×SSC).

In another more preferred embodiment of the present invention, the methyltransferase is an orphan DNA methyltransferase or part of a bacterial restriction modification system.

In yet another more preferred embodiment of the present invention, said methyltransferase is selected from M.Taql, M.Hhal, M.XbahI, M.PvuII, M.BsahI, M.FokI, M.BcnlB (M2.Bcnl), M.SssI, M.MpeI, M.PstI, M.XhoI, M.BseCI, M.M.Rsrl, M.EcoRI or a derivative thereof. However, any other methyltransferase with the same sequence specificity, i.e. with the same recognition sequence, or a reduced sequence specificity comprising only part of the recognition sequence of M.Taql, M.Hhal, M.BcnlB (M2.Bcnl), M.SssI, M.BseCI, M.Rsrl, M2.Bfil (M.BfiC2) and M2.Eco31 l could be useful for the methods of the present invention.

In another more preferred embodiment of the present invention, (a) the compound of formula (I) of the present invention or a derivative thereof blocks restriction enzyme cleavage at or near the recognition sequence of the DNA methyltransferase; and (b) methylation is detected by testing whether the modification of the DNA by said compound blocks cleavage mediated by a restriction enzyme at or near said recognition sequence. Any restriction enzyme and DNA methyltransferase mentioned in the present invention may be used when performing this method.

It has been observed by the inventor of the present invention that the presence of the compound of formula (I) of the present invention at the acceptor site of the recognition sequence blocks DNA cleavage by restriction enzymes with an overlapping or the same recognition sequence. Blocking restriction enzyme cleavage, as used herein, means preventing the restriction enzyme from cutting the DNA strands. Without being bound to theory, it is assumed that steric hindrance blocks accessibility of the recognition sequence so that the restriction enzyme can no longer bind to its target sequence in a productive manner. This observation can be exploited by assays which involve an initial labeling step with the compound of the present invention and a subsequent cleavage step with a restriction enzyme. Naturally, the choice of the restriction enzyme depends on the particular DNA methyltransferase employed in the labeling step. As a general guideline, the recognition sequence of the restriction enzyme should be nearby the modified base. Preferably, the recognition sequence of the restriction enzyme comprises the modified base. More preferably, the recognition sequence of the DNA methyltransferase and the recognition sequence of the restriction enzyme are the same. The choice of particular combinations of restriction enzyme and DNA methyltransferase is obvious to the skilled person and needs no further explanation. Moreover, the labeling reaction performed by the DNA methyltransferase and the restriction enzyme cleavage may be performed under standard conditions.

In yet another more preferred embodiment of the present invention, (a) the compound of formula (I) of the present invention or a derivative thereof interferes with nucleic acid amplification at the recognition site of the methyltransferase; and (b) methylation is detected by testing whether amplification of the nucleic acid molecule at the recognition site of the methyltransferase has been retarded.

Retardation of amplification may be achieved by interfering with primer binding or with strand elongation during an amplification reaction.

The term "amplification" or "amplify" means increase in copy number. The person skilled in the art knows various methods to amplify nucleic acid molecules, these methods may also be used in the present invention's method of diagnosing. Amplification methods include, but are not limited to, "polymerase chain reaction" (PCR), "ligase chain reaction" (LCR, EPA320308), "cyclic probe reaction" (CPR), "strand displacement amplification" (SDA, Walker et al., (1992) Nucleic Acid Res. 7, 1691-1696), "transcription based amplification systems" (TAS1 Kwoh et al., (1989) Proc. Nat. Acad. Sci. USA 86, 1173; Gingeras et al., PCT Application WO 88/10315). Preferably, amplification of DNA is accomplished by using polymerase chain reaction (PCR) [Methods in Molecular Biology, Vol. 226 (Bartlett and Stirling, eds.): PCR protocols, 2nd edition; PCR Technology: Principles and Applications for DNA Amplification (Erlich, ed.), New York 1992; PCR Protocols: A guide to methods and applications (Innis et al., eds.), Academic Press, San Diego 1990]. Nucleic acid amplification methods may be particularly useful in cases when the sample contains only minute amounts of nucleic acid. If said nucleic acid is RNA, an RT-PCR might be performed. Subsequently, another amplification step involving PCR may be performed. Alternatively, if said nucleic acid contained in the sample is DNA, PCR may be performed.

The PCR, generally, consists of many repetitions of a cycle which consists of: (a) a denaturing step, which melts both strands of a DNA molecule; (b) an annealing step, which is aimed at allowing the primers to anneal specifically to the melted strands of the DNA molecule; and (c) an extension step, which elongates the annealed primers by using the information provided by the template strand. Generally, PCR can be performed for example in a 50 μl reaction mixture containing 5 μL of 10×PCR buffer with 1.5 mM MgCl2, 200 μM of each deoxynucleoside triphosphate, 0.5 μL of each primer (10 μM), about 10 to 100 ng of template DNA and 1 to 2.5 units of Taq DNA Polymerase. The primers for the amplification may be labeled or be unlabeled. DNA amplification can be performed, e.g. with a model 2400 thermal cycler (Applied Biosystems, Foster City, Calif.): 2 min at 940 C1 followed by 35 cycles consisting of annealing (30 s at 5O0 C), extension (1 min at 72° C.), denaturing (10 s at 94° C.) and a final annealing step at 55° C. for 1 min as well as a final extension step at 72° C. for 5 min. However, the person skilled in the art knows how to optimize these conditions for the amplification of specific nucleic acid molecules or to scale down or increase the volume of the reaction mix.

A further method of nucleic acid amplification is the "reverse transcriptase polymerase chain reaction" (RT-PCR). This method is used when the nucleic acid to be amplified consists of RNA. The term "reverse transcriptase" refers to an enzyme that catalyzes the polymerization of deoxyribonucleoside triphosphates to form primer extension products that are complementary to a ribonucleic acid template. The enzyme initiates synthesis at the 3' end of the primer and proceeds toward the 5' end of the template until synthesis terminates. Examples of suitable polymerizing agents that convert the RNA target sequence into a complementary, copy-DNA (cDNA) sequence are avian myeloblastosis virus reverse transcriptase and *Thermus thermophilus* DNA polymerase, a thermostable DNA polymerase with reverse transcriptase activity marketed by Perkin Elmer. Typically, the genomic RNA/cDNA duplex template is heat denatured during the first denaturation step after the initial reverse transcription step leaving the DNA strand available as an amplification template. Suitable polymerases for use with a DNA template include, for example, *E. coli* DNA polymerase I or its Klenow fragment, T.sub.4 DNA polymerase, Tth polymerase, and Taq polymerase, a heat-stable DNA polymerase isolated from *Thermus aquaticus* and developed and manufactured by Hoffmann-La Roche and commercially available from Perkin Elmer. The latter enzyme is widely used in the amplification and sequencing of nucleic acids. The reaction conditions for using Taq DNA polymerase are known in the art and are described, e.g. in: PCR Technology, Erlich (1989, Stockton Press, New York; or in: Innis, Gelfand, Sninsky and White. 1990, PCR Protocols: A guide to methods and applications. Academic Press, New York. High-temperature RT provides greater primer specificity and improved efficiency. Copending U.S. patent application Ser. No. 07/746,121, filed Aug. 15, 1991, describes a "homogeneous RT-PCR" in which the same primers and polymerase suffice for both the reverse transcription and the PCR amplification steps, and the reaction conditions are optimized so that both reactions occur without a change of reagents. *Thermus thermophilus* DNA polymerase, a thermostable DNA polymerase that can function as a reverse transcriptase, can be used for all primer extension steps, regardless of template. Both processes can be done without having to open the tube to change or add reagents; only the temperature profile is adjusted between the first cycle (RNA template) and the rest of the amplification cycles (DNA template). The RT reaction can be performed, for example, in a 20 μl reaction mix containing: 4 μl of 5×ANV-RT buffer, 2 μl of oligo dT (100 μg/mL), 2

μl of 10 mM dNTPs, 1 μl total RNA, 10 units of AMV reverse transcriptase, and H$_2$O to 20 μl final volume. The reaction may be, for example, performed by using the following conditions: The reaction is held at 7O0 C for 15 minutes to allow for reverse transcription. The reaction temperature is then raised to 95° C. for 1 minute to denature the RNA-cDNA duplex. Next, the reaction temperature undergoes two cycles of 950 C for 15 seconds and 600 C for 20 seconds followed by 38 cycles of 9O0 C for 15 seconds and 60° C. for 20 seconds. Finally, the reaction temperature is held at 600 C for 4 minutes for the final extension step, cooled to 150 C, and held at that temperature until further processing of the amplified sample.

The term "primer" or "oligonucleotide", as used throughout the invention, refers to a short nucleic acid molecule from about 8 to about 30, eventually to about 50 nucleotides in length, whether natural or synthetic, capable of acting as a point of initiation of nucleic acid synthesis under conditions in which synthesis of a primer extension product complementary to a template nucleic acid strand is induced, i.e., in the presence of four different nucleoside triphosphates or analogues thereof and an agent for polymerisation (i.e., DNA polymerase or reverse transcriptase) in an appropriate buffer and at a suitable temperature. Preferably, a primer is a single-stranded oligodeoxyribonucleotide. The appropriate length of a primer depends on the intended use of the primer but typically ranges for PCR primers and primers used in sequencing reactions from 10 to 25 nucleotides. Short primer molecules generally require cooler temperatures to form sufficiently stable hybrid complexes with the template. A primer need not reflect the exact sequence of the template but must be sufficiently complementary to hybridize specifically with a template, provided its ability to mediate amplification is not compromised. "Hybridize" refers to the binding of two single-stranded nucleic acids via complementary base pairing, i.e. A to T (in RNA: U), G to C. The term "primer pair" refers to two primers that hybridize with the plus and minus strand, respectively, of a double-stranded nucleic acid molecule, and allow the amplification of e.g. DNA fragments, as for example in a PCR reaction. A primer can be labeled, if desired, by incorporating a compound detectable by spectroscopic, photochemical, biochemical, immunochemical, or chemical means. For example, useful labels include, but are not limited to, fluorescent dyes, electron-dense reagents, biotin, or small peptides for which antisera or monoclonal antibodies are available. A label can also be used to "capture" the primer, so as to facilitate a selection of amplified nucleic acid or fragments thereof. Carboxyfluorescein (FAM) and 6-carboxy-X-rhodamine (ROX) are preferred labels. However, other preferred labels include fluorochromes, e.g. fluorescein isothiocyanate (FITC), Texas Red, phycoerythrin, allophycocyanin, 6-carboxyfluorescein (6-FAM), 2',7'-dimethoxy-4I,5'-dichloro-6-carboxyfluorescein (JOE), 5-carboxyfluorescein (5-FAM) or N.N.N'.N'-tetraethyl-O-carboxyrhodamine, radioactive labels, e.g. 32P, 35S, 3H; etc.

The label may also be a two stage system, where the primer is conjugated to biotin, haptens, etc. having a high affinity binding partner, e.g. avidin, specific antibodies, etc., where the binding partner is conjugated to a detectable label. The label may be conjugated to one or both of the primers.

During said method for diagnosing, a step of nucleic acid sequencing may be performed. Any methods known in the art may be used for sequencing.

Preferably, the nucleic acid sequence is determined by a method based on the sequencing techniques of Sanger or Maxam/Gilbert (see for example: Methods inMolecular Biology, Vol. 167 (Graham and Hill, eds.): DNA sequencing protocols.2nd edition, 2001; Galas and McCormack, Genomic Technologies: Present and Future. Caister Academic Press, Wymondham, U K, 2002).

In a preferred embodiment of the present invention, PCR is real-time PCR. In another preferred embodiment of the present invention, nucleic acid amplification is carried out by real-time PCR.

In yet another more preferred embodiment of the present invention, (a) the compound of formula (I) of the present invention or a derivative thereof contains a fluorescent label; and (b) methylation is detected by measuring the presence or amount of fluorescence in said nucleic acid molecule. Said compound of formula (I) of the present invention or a derivative thereof may be labeled with any of the fluorescent labels mentioned in the present invention or known to the skilled artisan. In accordance with the present invention, Alexa, BODIPY, bimane, coumarin, Cascade blue, dansyl, dapoxyl, fluorescein, mansyl, MANT, Oregon green, pyrene, rhodamine, Tokyo Green, Texas red, ATTO, fluorescent nanocrystals (quantom dots), a cyanine fluorophore and derivatives thereof are particularly preferred labels.

"Measuring the presence or amount of fluorescence" means assessing whether, or not or how much fluorescence can be detected by fluorescence spectroscopy.

In another more preferred embodiment of the present invention, (a) nucleic acid molecules modified at the methyltransferase recognition sequence are purified by affinity purification; and (b) the compound of formula (I) of the present invention or a derivative thereof contains an affinity tag.

Nucleic acid molecules may be purified by using a compound capable of specifically binding to the label of compound of formula (I) of the present invention or a derivative thereof. In that case the label corresponds to or comprises an affinity tag. An affinity tag may be combined with one or more fluorescent labels. Preferably, the compound capable of binding to the label or affinity tag is an antibody, a protein, a peptide or an aptamer, wherein binding of these compounds is specific. The affinity tag may be an epitope such as the flag-tag, c-myc-tag, HA-tag, digoxygenin or dinitrophenol. Alternatively, the affinity tag may be an artificial peptide such as the His tag. "His tags" may be selected from His4>His5, His6) His7, His8, Hisg, His-io, His-n, Hisi2, Hisi3, His-u, HiSi5. Moreover, the affinity tag may be biotin, strep-tag, glutathione, nickel-nitrilotriacetic acid (NTA) or maltose. If the affinity tag is a "His tag", nickel coupled to a solid support may be used for purification. If the affinity tag is an epitope, an antibody-affinity coupled to a solid support may be used for purification. If the affinity tag is biotin or strep-tag, avidin or streptavidin or the like bound to a solid support may be used for purification. If the affinity tag is glutathione, glutathione transferase (GST) bound to a solid support may be used for purification. If the affinity tag is maltose, maltose binding protein bound to a solid support may be used for purification. If the affinity tag is nickel-nitrilotriacetic acid (NTA), a peptide containing several histidine residues bound to a solid support may be used for purification.

Affinity purification generally involves the separation of molecules in solution (mobile phase) based on differences in binding interaction with a ligand that is immobilized to a stationary material (solid phase). A support or matrix in affinity purification is any material to which a ligand may be covalently attached. Typically, the material to be used as an affinity matrix is insoluble in the system in which the target molecule is found. Usually, but not always, the insoluble matrix is solid. Hundreds of substances have been described and employed as affinity matrices. Useful affinity supports are those with a high surface area to volume ratio, chemical groups that are easily modified for covalent attachment of ligands, minimal nonspecific binding properties, good flow characteristics and mechanical and chemical stability. Preferred solid supports are agarose, sepharose and polystyrene beads.

Preferably, affinity purification is performed by using biotin, digoxygenin, glutathione or nickel-nitrilotriacetic acid (NTA) as the affinity tag of the compound of formula (I) of the present invention or a derivative thereof.

In another more preferred embodiment of the present invention, the compound of formula (I) of the present invention or a derivative thereof is added to a cytosine residue and cannot be added to a 5-methylcytosine residue in DNA.

In a preferred embodiment of the present invention, the method comprises after step (a) the additional step of sequencing the DNA molecule. Any methods known in the art may be used for sequencing. Preferably, the nucleic acid sequence is determined by a method based on the sequencing techniques of Sanger or Maxam/Gilbert (see for example: Methods in Molecular Biology, Vol. 167 (Graham and Hill, eds.): DNA sequencing protocols. 2nd edition, 2001; Galas and McCormack, Genomic Technologies: Present and Future. Caister Academic Press, Wymondham, U K, 2002).

In another preferred embodiment of the present invention, the label of said detectable cofactor is detected by (a) an antibody specifically binding to the label of said detectable cofactor or by (b) avidin or streptavidin specifically binding to the label of said detectable cofactor.

The term "antibody", as used throughout the invention, refers to monoclonal antibodies, polyclonal antibodies, chimeric antibodies, single chain antibodies, or a fragment thereof. Preferably the antibody is specific for its epitope. The antibodies may be humanized antibodies, synthetic antibodies, antibody fragments, such as Fab, F(ab2)', Fv or scFv fragments etc., or a chemically modified derivative of any of these. Monoclonal antibodies can be prepared, for example, by the techniques as originally described in Kohler and Milstein, (1975) Nature 256, 495, and Galfre, (1981) Meth. Enzymol. 73, 3, which comprise the fusion of mouse myeloma cells to spleen cells derived from immunized mammals with modifications developed by the art. Furthermore, antibodies or fragments thereof can be obtained by using methods which are described, e.g. in Harlow and Lane "Antibodies, A Laboratory Manual", CSH Press, Cold Spring Harbor, 1998. When derivatives of said antibodies are obtained by the phage display technique, surface plasmon resonance as employed in the BIAcore system can be used to increase the efficiency of phage antibodies which bind to an epitope to be analyzed (Schier, (1996) Human Antibodies Hybridomas 7, 97-105; Malmborg, (1995) J. Immunol. Methods 183, 7-13). The production of chimeric antibodies is described, for example, in WO89/09622.

Antibodies may be labelled, wherein the label may be any of the labels mentioned in the present invention.

Finally, in another preferred embodiment of the present invention, the identity of said DNA molecule is determined by DNA sequencing, hybridization, Maldi-Tof or analysis of nucleoside composition by enzymatic fragmentation and chromatography.

The invention is further illustrated by the following examples without being restricted to these examples.

Figure 6:
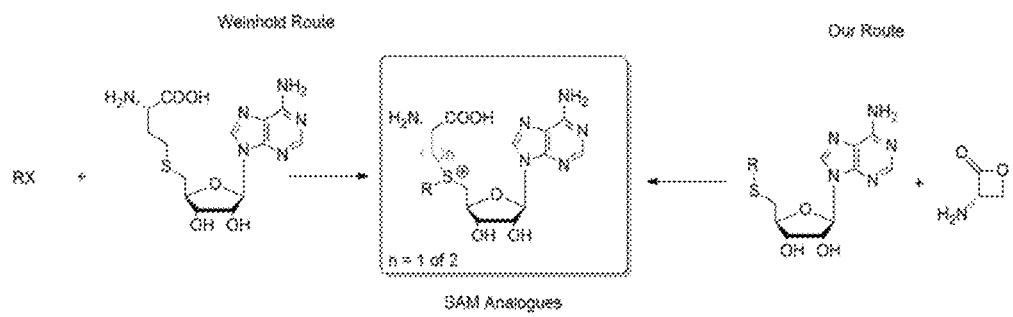
FIG. 6 shows a comparison of synthesis of prior art compounds and compounds (upper portion) and a comparison of the yields that can be obtained (lower portion) according to embodiments of the present invention. The yield for the compounds obtained also is shown.
Figure 6:
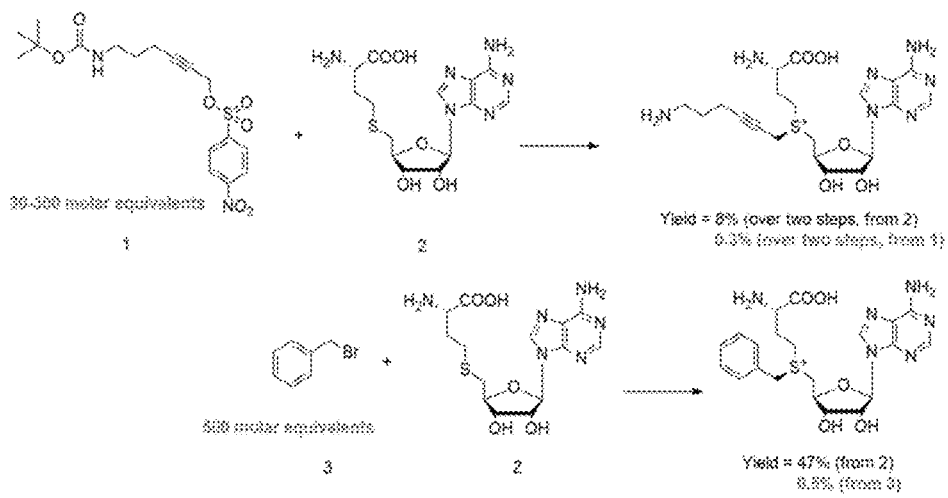
Figure 6:
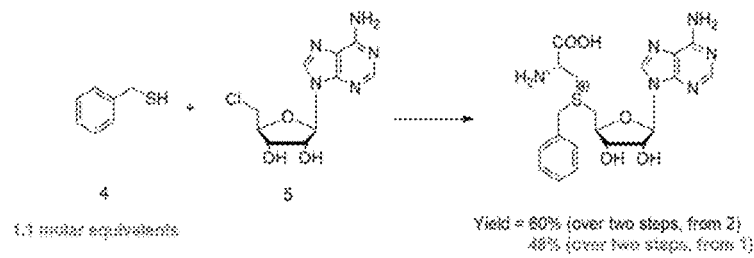
Figure 6:
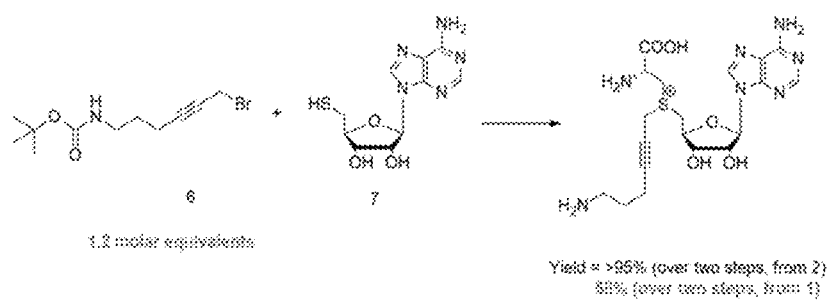

In one aspect, the present invention also relates to the synthesis of a compound as described above. The method of synthesis is based on the coupling of a thioether with a lactone. It is an advantage of embodiments of the present invention that the cofactors can be made with high efficiency, compared to at least some known prior art cofactors. The method allows for example direct synthesis of a fluorescent cofactor. By way of illustration FIG. 6 (upper portion) shows a comparison between exemplary synthesis methods of the cofactors described in U.S. Pat. No. 8,008,007 B2 and the synthesis used for making compounds according to embodiments of the present invention. Specific examples of yields obtained for different exemplary synthesis methods are shown in FIG. 6 (lower portion). It is to be noticed that the yield that can be obtained without the need for providing a large overshoot (e.g. with less than 2 molecular equivalents) of the functional group that is to be transferred afterwards when using the co-factor can be 50% or higher. Even if a large overshoot of equivalents is provided in the synthesis of known compounds from prior art (e.g. as described in U.S. Pat. No. 8,008,007), the yield still does not reach the yield obtained when synthesising the compounds according to embodiments of the present invention.

EXAMPLES

General Reaction Scheme for Synthesis of Cofactor Compounds:

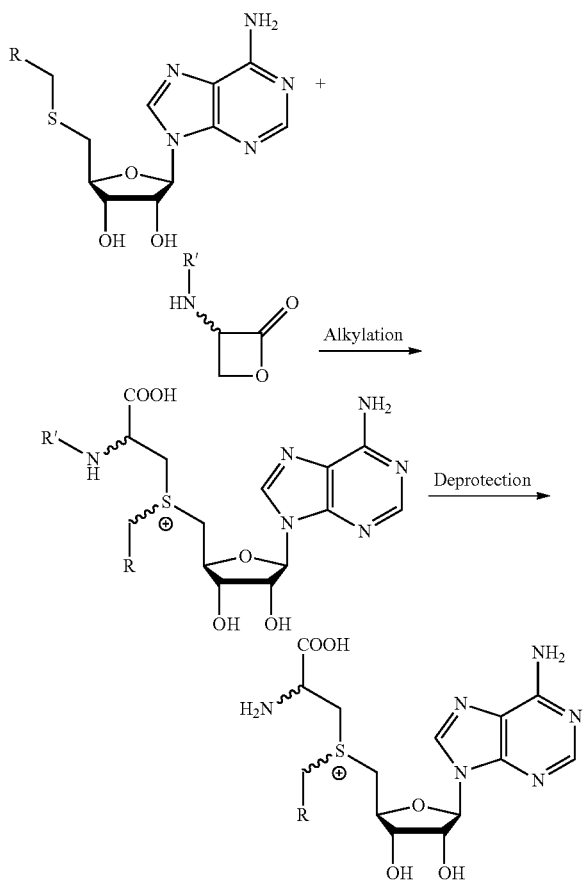

HPLC conditions: Solvent A: Methanol gradient in 20 mM ammonium formate; 20% to 100% over 30 minutes;

Solvent B: Methanol gradient in 20 mM ammonium formate; 0% to 30% over 20 minutes, increased to 60% over 10 minutes and increased to 100% over 2 minutes; Solvent C: Methanol gradient in 20 mM ammonium formate; 0% to 20% over 30 minutes, increased to 100% over 10 minutes.

Example 1: (Benzyl)(5'-Deoxyadenosyl)-(N-Boc-L-Cysteine)sulfonium Salt

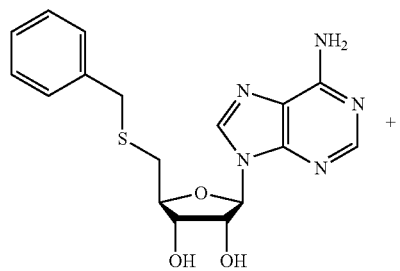

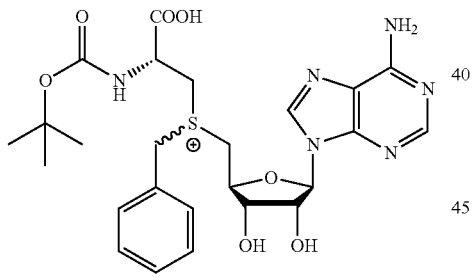

Chloroadenosine (5.71 g, 20 mmole) was charged into a roundbottom flask, and suspended in ethanol (100 ml). Potassium carbonate (5.52 grams, 40 mmoles, 2 equivalents, finely ground) was added. Oxygen was removed by flushing with nitrogen under sonication. Benzyl thiol (2.82 ml, 24 mmole, 1.2 equivalents) was added under oxygen free conditions, and the resulting mixture was heated to reflux for 3 hours, when TLC analysis indicated complete reaction. The reaction mixture was filtered while hot and the supernatant was allowed to cool to room temperature. The solvent was removed in vacuo and the resulting white solid, 5'-Deoxy-5'-(benzylthio)adenosine, was purified by crystallization from 2-propanol. Yield 91%. $^1$H-NMR δ 8.34 (s, 1H), 8.14 (s, 1H), 7.31-7.18 (m, 7H), 5.88 (d, 1H), 5.51 (d, 1H), 5.31 (d, 1H), 4.75 (q, 1H), 4.17 (m, 1H), 4.02 (m, 1H), 3.73 (s, 2H), 2.86-2.64 (dq, 2H). ESI-MS: 374.1 (M+H$^+$).

The 5'-Deoxy-5'-(benzylthio)adenosine (37 mg, 0.1 mmole) was suspended in formic acid (100 μl), followed by the addition of N-Boc-L-serine β-lactone (28 mg, 1.5 equivs.). The reaction was flushed with nitrogen and stirred at room temperature for two hours. The solvent was removed under vacuum at 30° C., and purified chromatographically (HPLC, solvent A): diastereomers of product at 24.8 min. and 25.4 min, starting material at 29.8 min. ESI-MS 562 (M+H$^+$). Yield: 48%.

Example 2: (Allyl)(5'-Deoxyadenosyl)-(N-Boc-L-Cysteine)sulfonium Salt

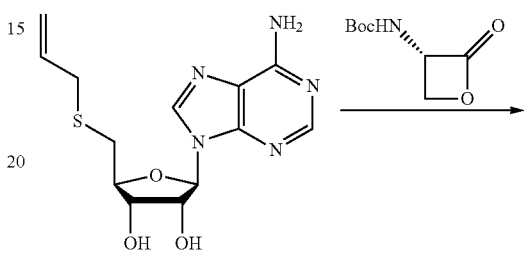

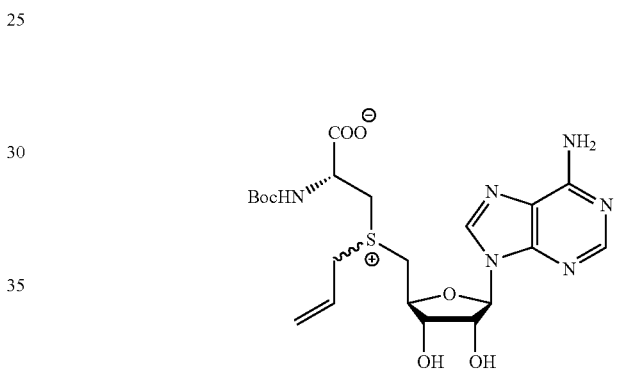

Chloroadenosine (2.85 g, 10 mmole) was charged into a roundbottom flask, and suspended in water (50 ml). Sodium hydroxide (1.6 gram, 40 mmoles, 2 equivalents) was added. Oxygen was removed by flushing with nitrogen under sonication. Allyl thiol (1.41 ml of a purity of 70%, 12 mmole, 1.2 equivalents) was added under oxygen free conditions, and the resulting mixture was heated to 60° C. for 90 minutes, when TLC analysis (CH$_2$Cl$_2$:MeOH; 9:1) indicated complete reaction. The reaction mixture was cooled to 0°-4° C. using an ice bath, and stirred for 15 minutes. The resulting precipitate is filtered, washed with water and dried in vacuum. The compound was of sufficient purity for further use. $^1$H-NMR (DMSO) δ 8.35 (s, 1H), 8.15 (s, 1H), 7.30 (s, 2H), 5.88 (d, 1H), 5.80-5.68 (m, 1H), 5.51 (d, 1H), 5.32 (d, 1H), 5.08-5.05 (m, 1H), 5.03 (s, 1H), 4.75 (m, 1H), 4.17 (m, 1H), 4.01 (m, 1H), 3.17 (m, 2.89-2.68). ESI-MS 324 (M+H$^+$).

The 5'-Deoxy-5'-(allylthio)adenosine (32 mg, 0.1 mmole) was suspended in formic acid (100 μl), followed by the addition of N-Boc-L-serine θ-lactone (28 mg, 1.5 equivs.). The reaction was flushed with nitrogen and stirred at room temperature for two hours. The solvent was removed under vacuum at 30° C., and purified chromatographically (HPLC, solvent A): diastereomers of product at 20.2 min. and 20.8 min, starting material at 25.5 min. ESI-MS 511 (M+H$^+$). Yield: 29%.

Example 3: (8-Azido-oct-2-ene)(5'-Deoxyadenosyl)-(N-Boc-L-Cysteine)sulfonium Salt

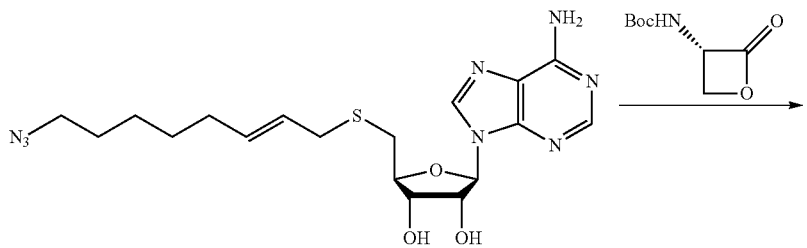

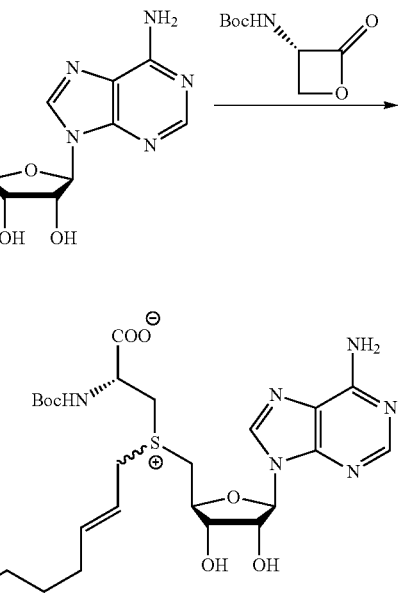

S-(E)-8-azido-oct-2-ene-5'-thioadenosine is prepared by heating 5'-thioadenosine (141 mg, 0.5 mmole, see Pignot et al., Eur. J. Org. Chem, 2000, 549 for synthesis), (E)-8-azido-1-bromooct-2-ene (127 mg, 0.55 mmole), and NaOCH$_3$ (30 mg, 0.55 mmole) in CH$_3$OH (10 ml) at 70° C. for 3 h, followed by evaporation and chromatographic purification (Silica, CH$_2$Cl$_2$:MeOH 9:1). The compound is obtained as a colorless foam in 58% yield. $^1$H-NMR (CD$_3$OD) δ 8.30 (s, 1H), 8.20 (s, 1H), 5.99 (d, 1H), 5.38 (m, 2H), 4.77 (m, 1H), 4.34 (m, 1H), 4.16 (m, 1H), 3.23-3.04 (m, 4H), 2.87 (m, 2H), 1.98 (m, 2H), 1.51 (m, 2H), 1.32 (m, 4H), MS (ESI) 434.2 (M+H$^+$).

The S-(E)-8-azido-oct-2-ene-5'-thioadenosine (88 mg, 0.2 mmole) was suspended in formic acid (100 μl), followed by the addition of N-Boc-L-serine β-lactone (56 mg, 1.5 equivs.). The reaction was flushed with nitrogen and stirred at room temperature for two hours. The solvent was removed under vacuum at 30° C., and purified chromatographically (HPLC, solvent A): diastereomers of product at 29.8 min. and 30.1 min, starting material at 34.8 min. ESI-MS 622.2 (M+H$^+$). Yield: 64%

Example 4: (6-Azido-hex-2-yne)(5'-Deoxyadenosyl)-(N-Boc-L-Cysteine)sulfonium Salt

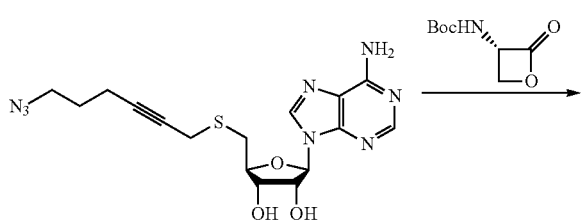

-continued

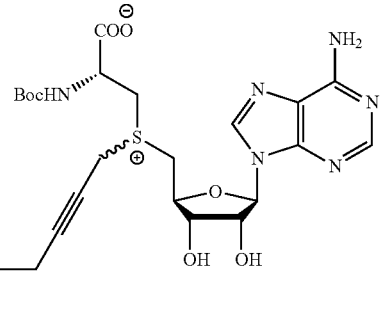

S-6-azido-hex-2-yne-5'-thioadenosine is prepared by heating 5'-thioadenosine (142 mg, 0.5 mmole, see Pignot et al., Eur. J. Org. Chem, 2000, 549 for synthesis), 6-azido-1-bromohex-2-yne (162 mg, 0.8 mmole), and NaOCH$_3$ (43 mg, 0.8 mmole) in DMF (4 ml) at 70° C. for 3 h, followed by evaporation and chromatographic purification (Silica, CH$_2$Cl$_2$:MeOH 9:1). The compound is obtained as colorless foam. Yield: 74%. $^1$H-NMR (CD$_3$OD) δ 8.32 (s, 1H), 8.23 (s, 1H), 6.02 (d, 1H), 5.38 (m, 2H), 4.80 (t, 1H), 4.36 (t, 1H), 4.27 (dd, 1H), 3.40 (t, 2H), 3.15-3.01 (m, 2H), 2.33-2.27 (m, 2H), 1.72 (m, 2H) MS (ESI) 405.5 (M+H$^+$).

The S-6-azido-hex-2-yne-5'-thioadenosine (40 mg, 0.1 mmole) was suspended in formic acid (100 μl), followed by the addition of N-Boc-L-serine β-lactone (28 mg, 1.5 equivs.). The reaction was flushed with nitrogen and stirred at room temperature for two hours. The solvent was removed under vacuum at 30° C., and purified chromatographically (HPLC, solvent A): diastereomers of product at 25.8 min. and 26.1 min, starting material at 29.7 min. ESI-MS 492.2 (M+H$^+$). Yield: 56%

Example 5: (6-Amino-hex-2-yne)(5'-Deoxyadenosyl)-(N-Boc-L-Cysteine)sulfonium Salt

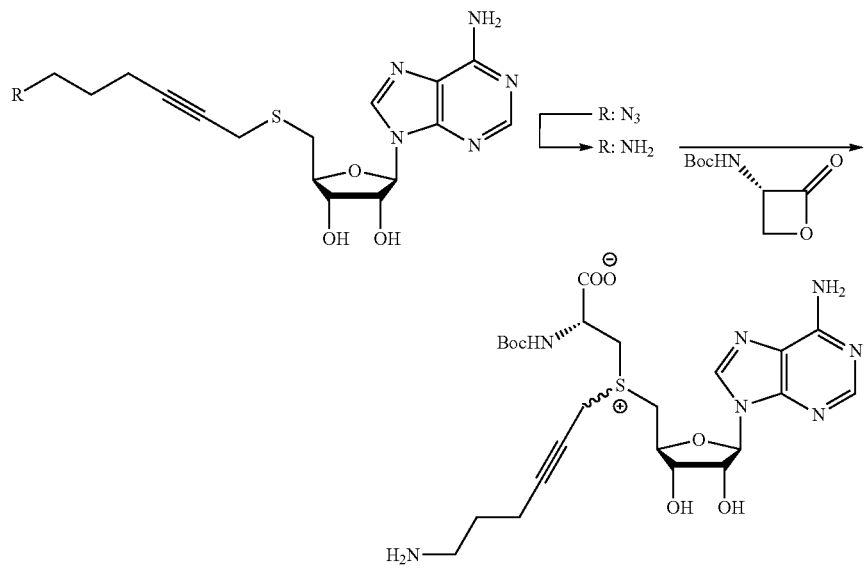

S-6-amino-hex-2-yne-5'-thioadenosine is prepared by heating S-6-azido-hex-2-yne-5'-thioadenosine (404 mg, 1 mmole, see example 4) in a THF:$H_2O$ (10 ml, 5 ml) mixture in the presence of triphenylphospine (314 mg, 1.2 mmole) at reflux for 3 h, followed by evaporation and chromatographic purification (Silica pad, $CH_2Cl_2$:MeOH 7:3). The compound is obtained as colorless foam. Yield: 74%.$^1$H-NMR (DMSO-$d_6$) δ 8.35 (s, 1H), 8.15 (s, 1H), 7.31 (s, 2H), 5.89 (d, 1H), 4.75 (t, 1H), 4.15 (t, 1H), 4.06 (dd, 1H), 3.05-2.87 (m, 2H), 2.72 (t, 2H), 2.29-2.23 (m, 2H), 1.62 (m, 2H), MS (ESI) 379.1 (M+H$^+$).

The S-6-amino-hex-2-yne-5'-thioadenosine (38 mg, 0.1 mmole) was suspended in formic acid (100 µl), followed by the addition of N-Boc-L-serine β-lactone (28 mg, 1.5 equivs.). The reaction was flushed with nitrogen and stirred at room temperature for two hours. The solvent was removed under vacuum at 30° C., and purified chromatographically (HPLC, solvent A): diastereomers of product at 17.0 min. and 17.6 min, starting material at 19.7 min. ESI-MS 566.2 (M+H$^+$). Yield: 27%

Example 6: (Ethyl Carboxymethyl)(5'-Deoxyadenosyl)-(N-Boc-L-Cysteine)sulfonium Salt

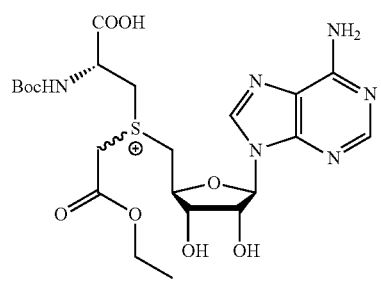

Chloroadenosine (2.85 g, 10 mmole) was charged into a roundbottom flask, and suspended in water (50 ml). Sodium hydroxide (1.6 gram, 40 mmoles, 4 equivalents) was added. Oxygen was removed by flushing with nitrogen under sonication. Ethyl mercaptoacetate (1.31 ml, 12 mmole, 1.2 equivalents) was added under oxygen free conditions, and the resulting mixture was heated to 80° C. for 150 minutes, when TLC analysis ($CH_2Cl_2$:MeOH; 9:1) indicated complete reaction. The reaction mixture was cooled to room temperature and the precipitate is filtered, washed with water (2×), cold ethanol (2×) and dried in vacuum. The compound was of sufficient purity for further use. $^1$H-NMR (DMSO-$d_6$) δ 8.33 (s, 1H), 8.14 (s, 1H), 7.30 (s, 2H), 5.88 (d, 1H), 5.52 (d, 1H), 5.33 (s, 2H), 4.72 (m, 1H), 4.17-4.00 (m, 4H), 3.40 (m, 2H), 3.03-2.88 (m, 2H), 1.14 (t, 3H).

The S-Ethylcarboxymethyl-5'-thioadenosine (38 mg, 0.1 mmole) was suspended in formic acid (100 µl), followed by the addition of N-Boc-L-serine β-lactone (28 mg, 1.5 equivs.). The reaction was flushed with nitrogen and stirred at room temperature for two hours. The solvent was removed under vacuum at 30° C., and purified chromatographically (HPLC, solvent A): diastereomers of product at 22.8 min. and 23.0 min, starting material at 23.7 min. ESI-MS 557.2 (M+H$^+$). Yield: 53%

Example 7: (Benzyl)(5'-Deoxyadenosyl)-(3-Propionate)sulfonium Salt

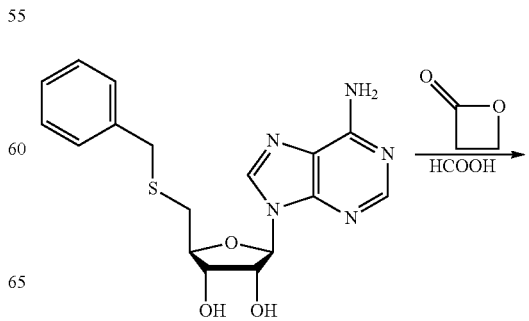

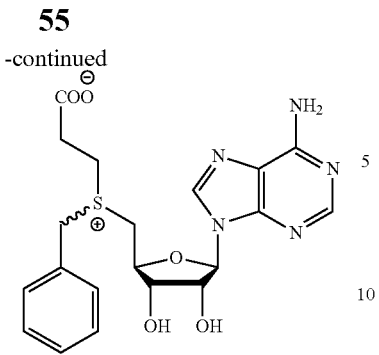

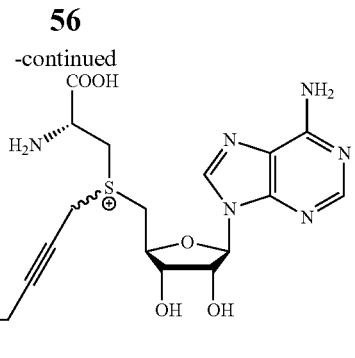

The 5'-Deoxy-5'-(benzylthio)adenosine (see Example 1, 37 mg, 0.1 mmole) was suspended in formic acid (100 μl), followed by the addition β-propiolactone (9.5 μl, 1.5 equivs.). The reaction was flushed with nitrogen and stirred at room temperature for two hours. The solvent was removed under vacuum at 30° C., resulting in the product as a colorless semi-solid of sufficient purity for further use. Retention time of product (HPLC solvent A): 3.99 min., starting material 29.22 min. ESI-MS 446.1 (M+H$^+$). Yield (Racemic): 93%.

Example 8: (Benzyl)(5'-Deoxy-N$^6$,N$^6$-dimethyladenosyl)-(N-Boc-L-Cysteine) Sulfonium Salt

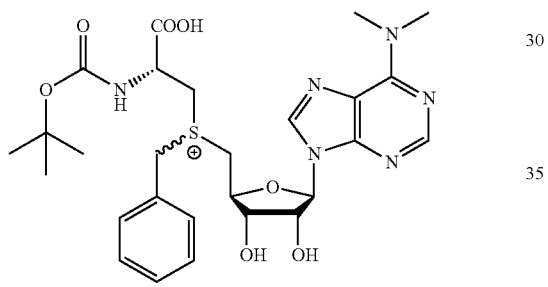

The 5'-Deoxy-5'-(benzylthio)-N$^6$,N$^6$-adenosine (38 mg, 0.1 mmole) was suspended in formic acid (100 μl), followed by the addition of N-Boc-L-serine β-lactone (28 mg, 1.5 equivs.). The reaction was flushed with nitrogen and stirred at room temperature for two hours. The solvent was removed under vacuum at 30° C., and purified chromatographically (HPLC, solvent A): diastereomers of product at 28.7 min. and 29.3 min, starting material 33.3 min. ESI-MS 589.2 (M+H$^+$). Yield: 46%

Example 9: (6-Azido-hex-2-yne)(5'-Deoxyadenosyl)-(L-Cysteine)sulfonium Salt

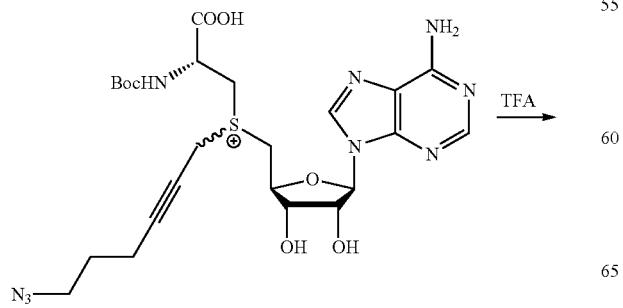

(6-Azido-hex-2-yne)(5'-Deoxyadenosyl)-(N-Boc-L-Cysteine)sulfonium salt (Racemic, 0.1 mmole scale, see example 4 for synthesis) is suspended in TFA (100 μl) an stirred at room temperature for 2 h. The trifluoroacetic acid is removed under reduced pressure and the crude product is purified chromatographically. Retention time of products (HPLC solvent A): 14.5 min. and 15.9 min. ESI-MS 492.2 (M+H$^+$). Yield: quant.

Example 10: (6-Amino-hex-2-yne)(5'-Deoxyadenosyl)-(L-Cysteine)sulfonium Salt

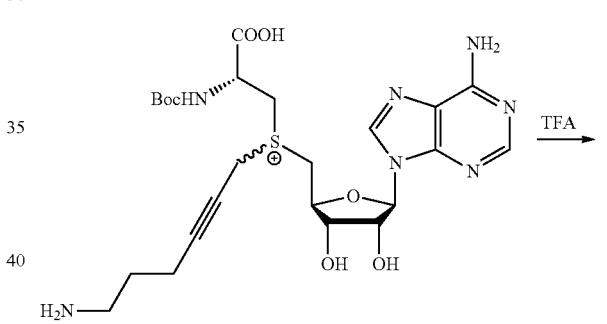

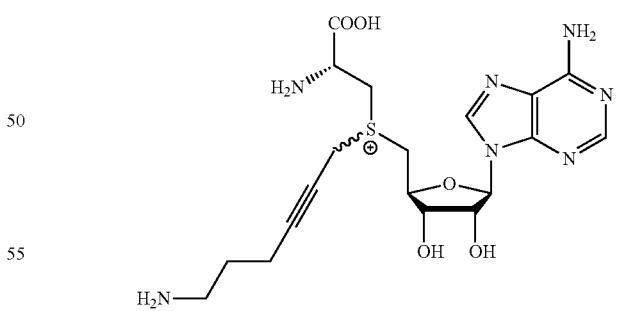

(6-Amino-hex-2-yne)(5'-Deoxyadenosyl)-(N-Boc-L-Cysteine)sulfonium salt (Racemic, 0.1 mmole scale, see example 5 for synthesis) is suspended in TFA (100 μl) an stirred at room temperature for 2 h. The trifluoroacetic acid is removed under reduced pressure and the crude product is purified chromatographically. Retention time of products (HPLC solvent B): 8.8 min. and 9.7 min. ESI-MS 466.2 (M+H$^+$). Yield: quant.

Example 11: Fluorescent Sulfonium Salt

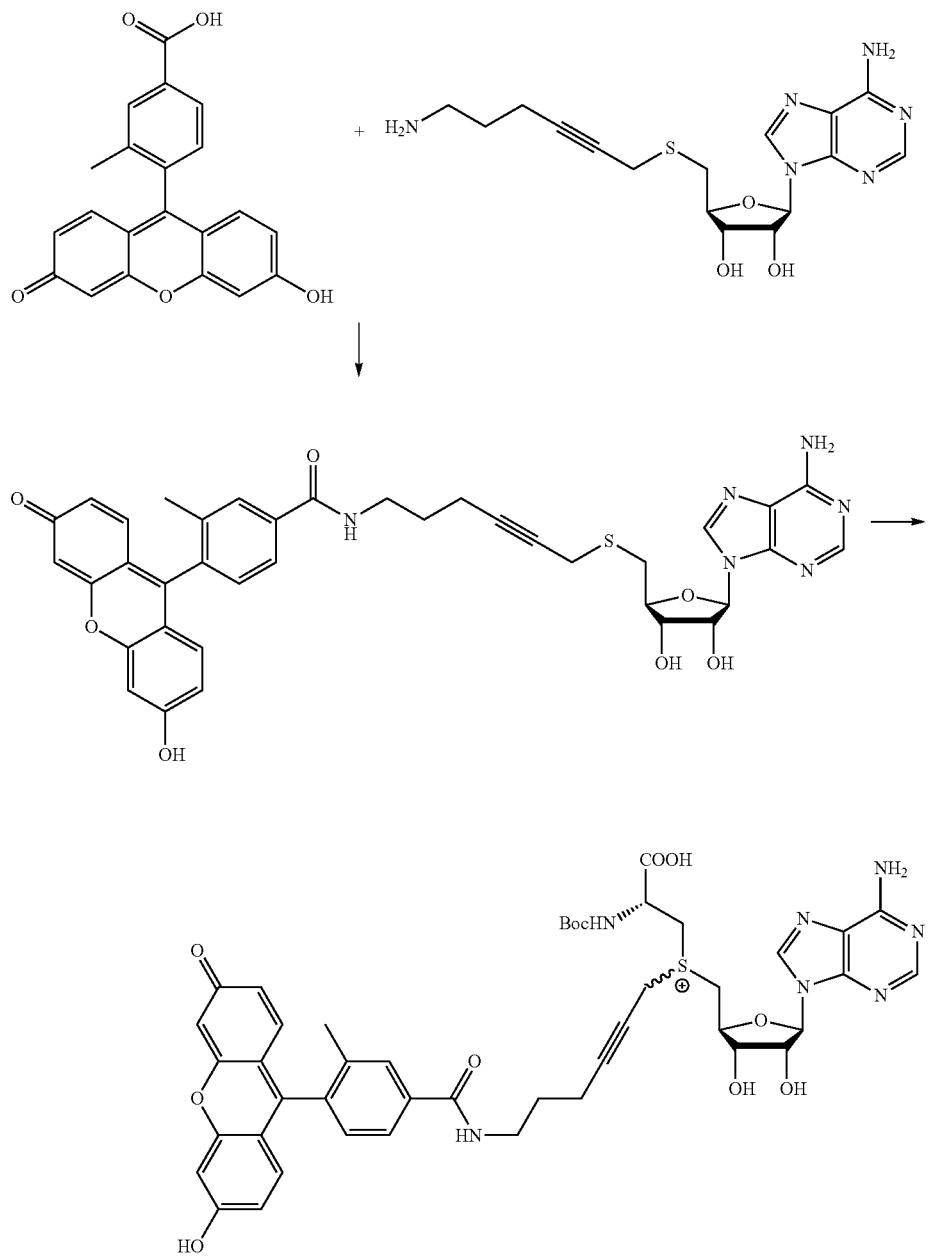

To Tokyo Green carboxylic acid (70 mg, 0.2 mmole, Urano et al. J. Am. Chem. Soc. 2005, 4888) in DMF is added EDCI (42 mg, 0.22 mmole, 1.1 equiv.) and NHS (25 mg, 0.22 mmole, 1.1 equivalent), and stirred for 60 minutes at room temperature, when TLC analysis indicates complete formation of the NETS-ester. (6-Amino-hex-2-yne)(5'-Deoxyadenosyl)-(N-Boc-L-Cysteine)sulfonium salt (76 mg, 0.2 mmole, see example 5 for synthesis) is added, and the reaction mixture is heated to 60° C. for 2 h and allowed to cool to room temperature overnight. The solvent is removed under reduced pressure, and the product is purified chromatographically (silica, $CH_2Cl_2$:MeOH 9:1 to 8:2). The product is isolated as an orange solid. Yield 80%. ESI-MS: 708.1 ($M+H^+$).

Tokyo Green-adenosine sulfide (70 mg, 0.1 mmol) is suspended in formic acid (200 μl), followed by the addition of N-Boc-L-serine β-lactone (28 mg, 1.5 equivs.). The reaction was flushed with nitrogen and stirred at room temperature for two hours. The formic acid is stripped; the resulting oil is resuspended in trifluoroacetic acid (100 μl), stirred at room temperature for 2.5 hours and stripped of volatiles again. The crude product is purified chromatographically (HPLC, solvent A). Boc protected product at 27.9 min. Diastereomers of final product at 25.8 and 26.6 min, starting material at 29.2 min. ESI-MS 894.3 (Boc product, $M+H^+$) 794.2 ($M+H^+$).

Example 12: Fluorescent Sulfonium Salt II

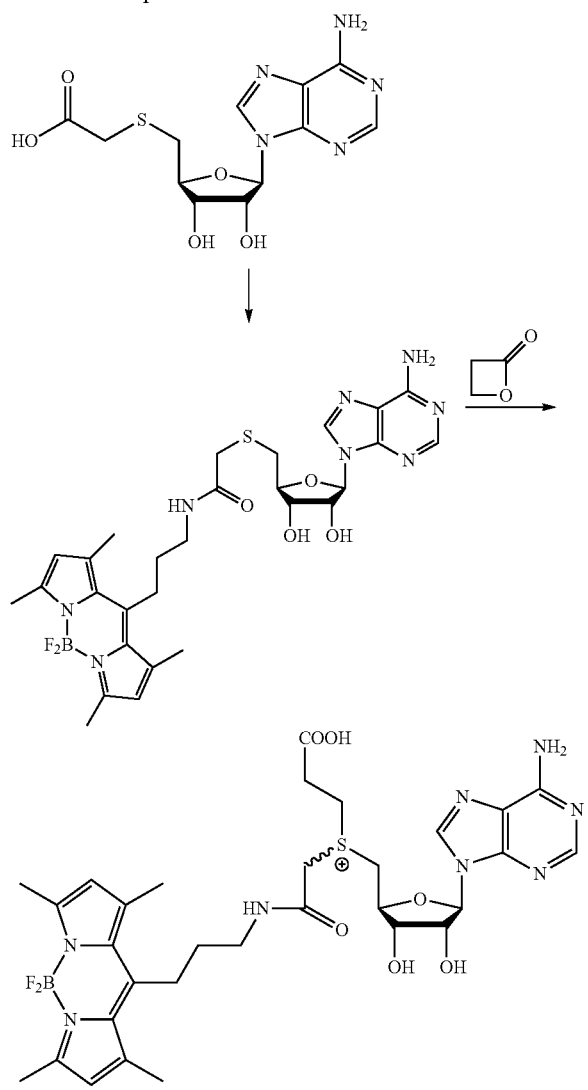

Chloroadenosine (5.71 g, 20 mmole) was charged into a roundbottom flask, and suspended in water (100 ml). Sodium hydroxide (1.920 grams, 48 mmoles, 2.2 equivalents) was added. Oxygen was removed by flushing with nitrogen under sonication. Mercapto acetic acid (1.67 ml, 24 mmole, 1.2 equivalents) was added under oxygen free conditions, and the resulting mixture was heated to 70° C. for 3 hours, when TLC analysis indicated complete reaction. The reaction mixture was cooled to room temperature, and carefully neutralized by the dropwise addition of concentrated hydrochloric acid. The resulting white solid was filtered, washed with cold ethanol and dried in air. Yield: 86%. 1H-NMR (DMSO) δ12.56 (s, br, 1H), 8.34 (s, 1H), 8.15 (s, 1H), 7.30 (s, 2H), 5.89-5.87 (m, 2H), 4.74 (q, 1H), 4.16 (m, 1H), 4.03 (m, 1H), 3.25 (s, 2H), 3.03-2.87 (m, 2H).

To S-Carboxymethyl-5'-thioadenosine (68 mg, 0.2 mmole) in DMF is added EDCI (42 mg, 0.22 mmole, 1.1 equiv.) and NHS (25 mg, 0.22 mmole, 1.1 equivalent), and stirred for 30 minutes at room temperature. 8-(3-aminopropyl)-1,3,5,7-tetramethyl BODIPY (61 mg, 0.2 mmole, dissolved in DMF (1 ml) is added and the resulting mixture is stirred overnight. The solvent is removed by evaporation under reduced pressure and the residue is purified chromatographically (Silica, $CH_2Cl_2$:MeOH 9:1). Yield: 67%. $^1$H-NMR ($CD_3OD$) δ 8.26 (s, 1H), 8.16 (s, 1H), 6.04 (s, 2H), 5.94 (d, 1H), 4.73 (t, 1H), 4.30 (m, 1H), 4.21 (m, 1H), 3.31-3.22 (m, 4H), 3.05-2.84 (m, 4H) 2.41 (s, 6H), 2.35 (s, 6H), 1.74 (m, 2H). ESI-MS: 629.2 ($M+H^+$), 652.8 (M+Na).

BODIPY-thioadenosine (63 mg, 0.1 mmole) is suspended in formic acid (100 µl), followed by the addition β-propiolactone (9.5 µl, 1.5 equivs.). The reaction was flushed with nitrogen and stirred at room temperature for four hours. The solvent was removed under vacuum at 30° C., resulting in the product as a red solid which was purified chromatographically. Retention time of product (HPLC solvent A): 29.99 min., starting material 32.7 min. ESI-MS 701.2 ($M+H^+$). Yield (Racemic): 42% (53% starting material recovered).

Example 12: Fluorescent Sulfonium Salt III

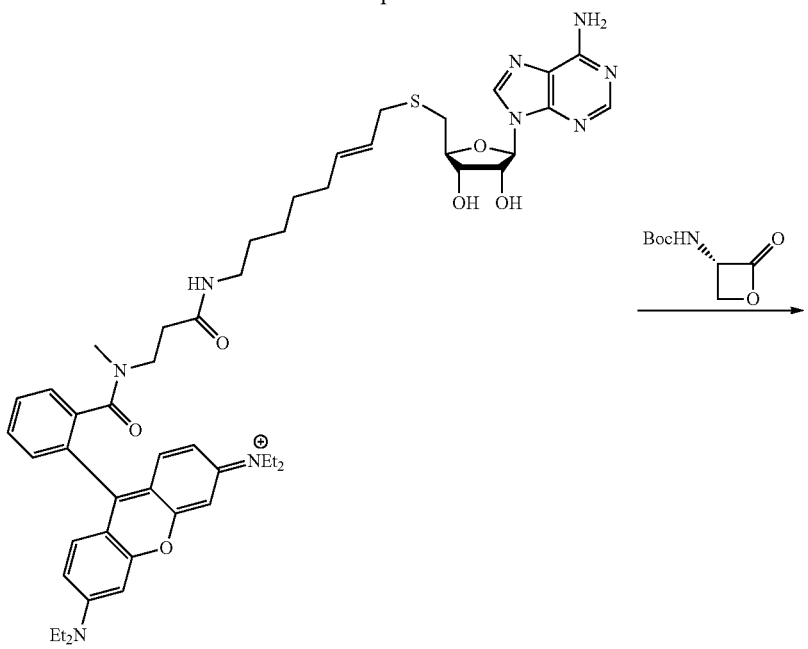

-continued

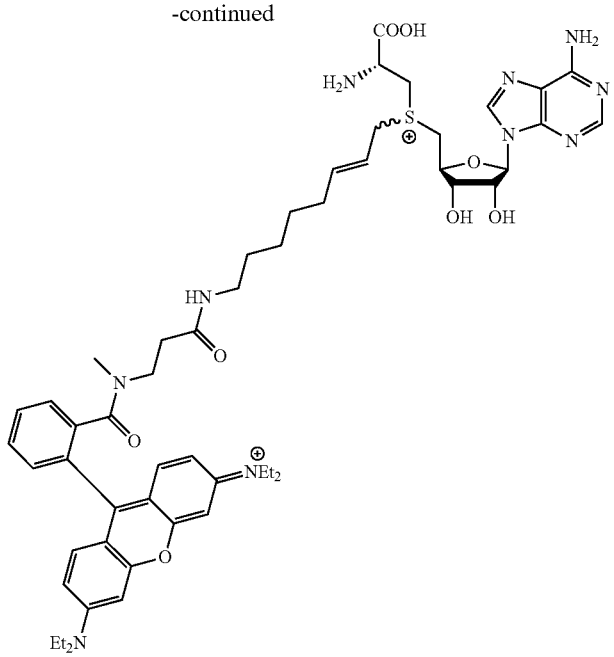

Rhodamine B-thioadenosine (90 mg, 0.1 mmole) is suspended in formic acid (100μl), followed by the addition N-Boc-L-serine β-lactone (28 mg, 1.5 equivs.). The reaction was flushed with nitrogen and stirred at room temperature for two hours. The formic acid is stripped; the resulting oil is resuspended in trifluoroacetic acid (100 μl), stirred at room temperature for 2.5 hours and stripped of volatiles again. Once complete conversion is observed using TLC analysis, the volaties are removed, and the crude product is purified by filtration over a RP-Silica pad. Yield 83%.

Example 13: Dethiobiotin Sulfonium Cofactor

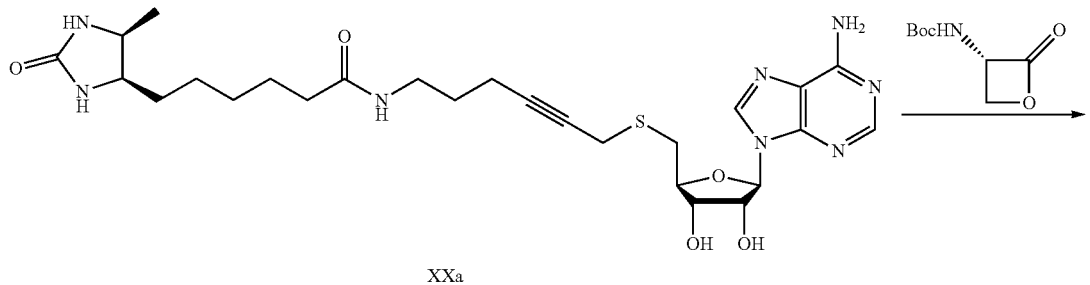

XXa

-continued

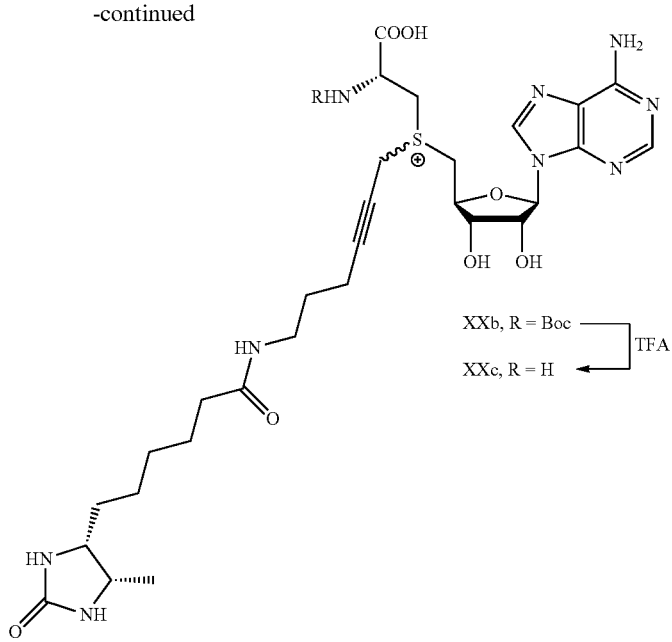

D-Dethiobiotin (0.15 mmole) is suspended in DMF (1 ml), followed by the addition of NHS (0.15 mmole) and EDCI (0.15 mmole). The resulting mixture is stirred for 60 minutes, followed by the addition of S-6-amino-hex-2-yne-5'-thioadenosine (0.14 mmole, see example 5 for preparation). The reaction is allowed to stir at room temperature overnight, when the solvent is removed in vacuo, and the crude compound is purified by filtration over a short silica plug ($CH_2Cl_2$:MeOH 9:1 to 8:2) to obtain the desired thioether as a clear oil. Yield 83%. ESI-MS: 597.4 ($M+Na^+$).

The oil is dissolved in formic acid and alkylated in accordance with the general procedure (N-Boc oxetanone, 1.5 equivalents) over 4 hours at room temperature. The formic acid is stripped; the turbid oil is resuspended in trifluoroacetic acid (100 µl), stirred at room temperature for 2.5 hours and stripped of volatiles again. The crude product is purified chromatographically (HPLC, solvent A). Diastereomers of product at 20.93 min. and 23.40 min, starting material at 27.21 min. ESI-MS: 662.3 ($M+H^+$). Yield: 30%

Example 14: Targeted Alkylation of DNA

Adenine-N6 DNA modification by M.TaqI DNA methyltransferase: M.TaqI DNA methyltransferase targets the four-base recognition sequence 5'-TCGA-3' and modifies the underlined adenine residue at the N6-position and was combined with (6-Azido-hex-2-yne)(5'-Deoxyadenosyl)-(L-Cysteine)sulfonium salt (see example 9 for preparation). The methyltransferase enzyme and cofactors were incubated with pUC19 DNA in "Cutsmart buffer" at 60° C. for 1 hour. To determine if protection occurred the DNA was incubated with the corresponding restriction enzyme (TaqaI) for 1 hour. Afterwards, the remaining proteins were digested with Proteinase K. The DNA samples are then placed on an agarose gel and visualized with Ethidium bromide (FIG. 1).

The protected controls show 1 band corresponding to uncut DNA. The cut controls show 3 bands corresponding to the cut fragments. The cofactor containing samples all show 1 strong band, corresponding to uncut DNA, thus proving that the synthetic cofactor serves as a substrate for the enzymatic labeling of DNA.

Example 15: Targeted Alkylation of DNA

Figure 3:
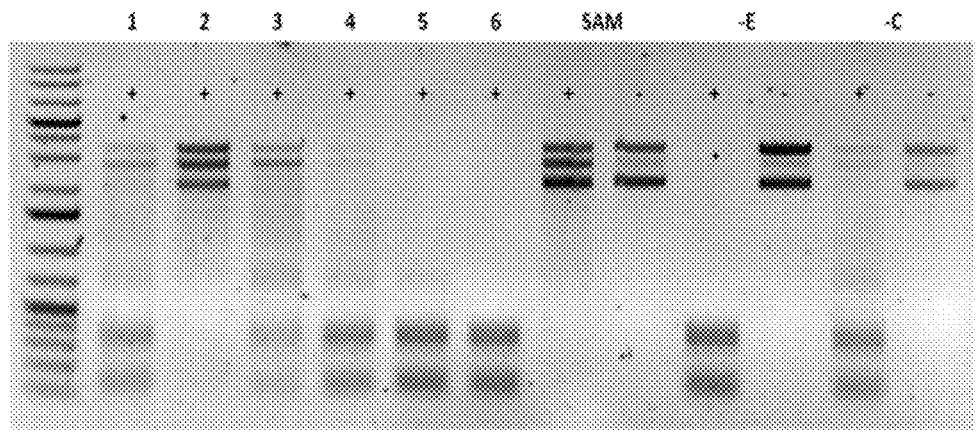
FIG. 3 shows the image of agarose gel, illustrating how incubation of DNA with cytosine methyltransferase enzyme (M.MpeI) and a synthetic cofactor results in the same protection as with the natural cofactor, against cutting by a restriction enzyme.

Cytosine DNA modification by M.MpeI DNA methyltransferase: M.TaqI DNA methyltransferase targets the two-base recognition sequence 5'-CG-3' and modifies the underlined cytosine residue and was combined with (8-Azido-oct-2-ene)(5'-Deoxyadenosyl)-(L-Cysteine)sulfonium salt (see example 9 for preparation). The methyltransferase enzyme and cofactors were incubated with pUC19 DNA in "Cutsmart buffer" at 60° C. for 1 hour. To determine if protection occurred the DNA was incubated with the corresponding restriction enzyme (HhaI) for 1 hour. Afterwards, the remaining proteins were digested with Proteinase K. The DNA samples are then placed on an agarose gel and visualized with Ethidium bromide (FIG. 3).

The protected controls show 1 band corresponding to uncut DNA. The cut controls show 3 bands corresponding to the cut fragments. The cofactor containing samples all show 1 strong band, corresponding to uncut DNA, thus proving that the synthetic cofactor serves as a substrate for the enzymatic labeling of DNA.

Example 18: Fluorescent Labeling of DNA

Figure 4:
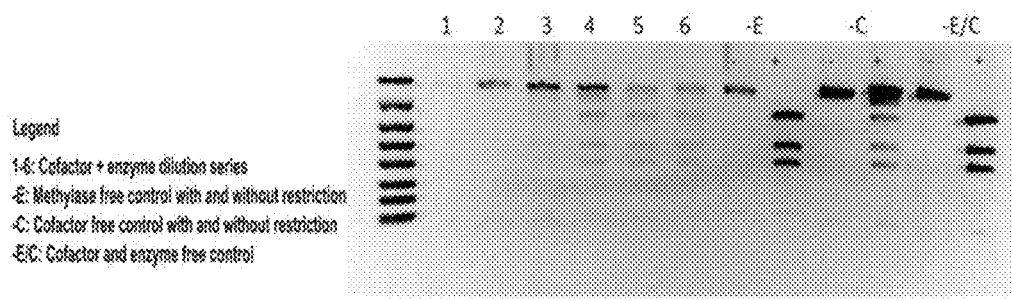
FIG. 4 shows the image of an agarose gel, illustrating how incubation of DNA with adenosine methyltransferase enzyme (M.TaqI) and a fluorescent synthetic cofactor results in the same protection as with the natural cofactor, against cutting by a restriction enzyme.

Adenine-N6 DNA modification by M.TaqI DNA methyltransferase: M.TaqI DNA methyltransferase targets the four-base recognition sequence 5'-TCGA-3' and modifies the underlined adenine residue at the N6-position and was combined with Rhodamine sulfonium salt (see example 12 for preparation). The methyltransferase enzyme and cofactors were incubated with pUC19 DNA in "Cutsmart buffer" at 60° C. for 1 hour. To determine if protection occurred the DNA was incubated with the corresponding restriction enzyme (TaqaI) for 1 hour. Afterwards, the remaining proteins were digested with Proteinase K. DNA samples are then placed on an agarose gel and visualized with Ethidium bromide (FIG. 4).

The protected controls show 1 band corresponding to uncut DNA. The cut controls show 3 bands corresponding to the cut fragments. The cofactor containing samples all show 1 strong band, corresponding to uncut DNA, slowly changing into the restricted pattern with decreasing concentration, thus proving that the synthetic cofactor serves as a substrate for the enzymatic labeling of DNA.

Figure 5:
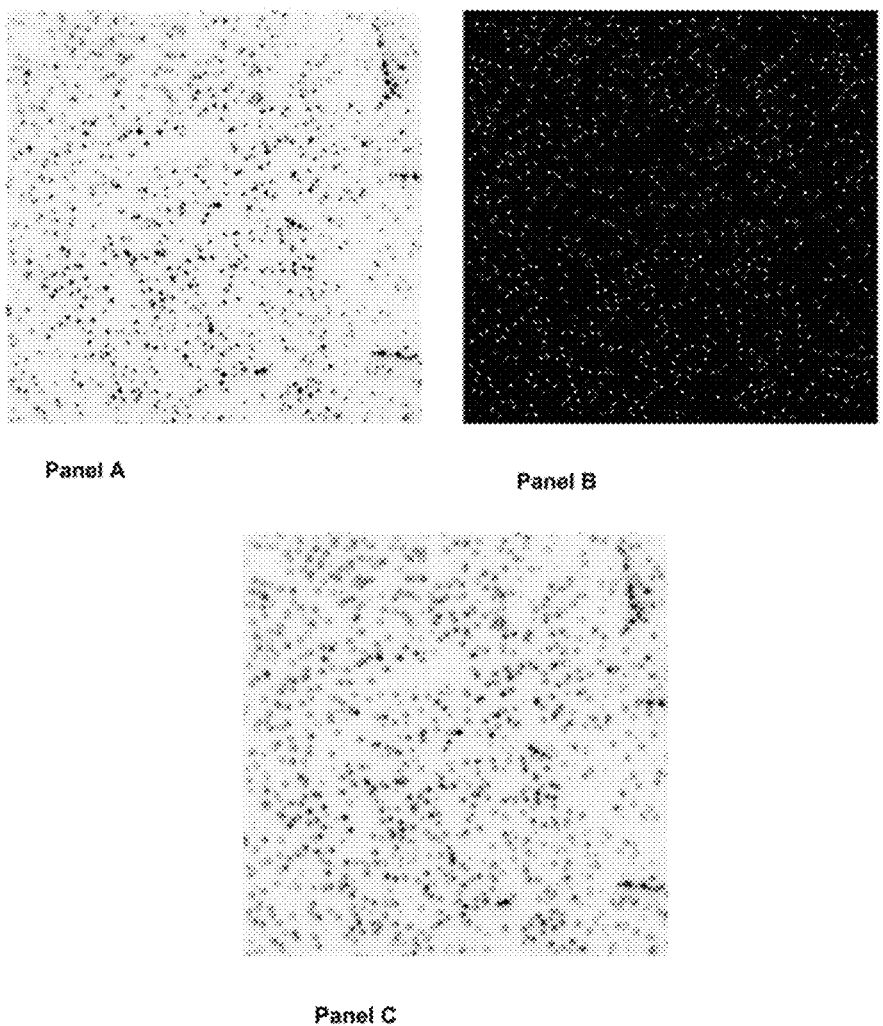
FIG. 5 shows fluorescent DNA in super resolution microscopy, with panel A showing the microscopy image, panel B an inverted image of the plasmid DNA and panel C show colocalization of the Rhodamine dye Fluoerescent Sulfonium Salt III with a DNA intercalating dye, indicating successful fluorescent DNA labeling.

Fluorescent DNA was purified using DNA Cleaner & Concentrator 5 columns (Zymo Research), and the DNA was spin coated on poly-L-lysine coated cover slips and used directly for microscopy studies. (FIG. 5)

The invention claimed is:

1. A compound represented by formula (I)

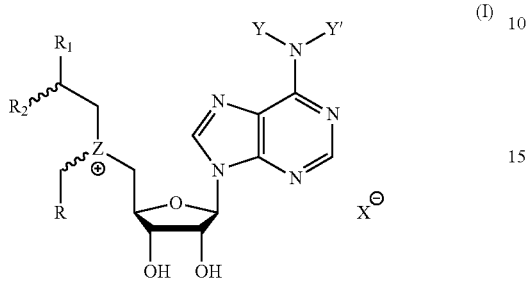

(I)

wherein

R1 is COOH or COO—;

X is an organic or inorganic anion carrying one or more negative charges;

Y and Y' are H, or an alkyl;

R2 is NH$_2$, NHBoc, or H; and

Z is S or Se

R comprises a carbon-carbon double bond, carbon-oxygen double bond, carbon-sulfur double bond, carbon-nitrogen double bond, a carbon-carbon triple bond, carbon-nitrogen triple bond, an aromatic carbocyclic or heterocyclic system in β-position to the sulfonium center, unsaturated c-c bond, or c-heteroatom bond where the heteroatom is O, N, S.

2. A compound according to claim 1, wherein R, R2, Y, and Y' are selected from the following:

| Y | Y' | R2 | R |
|---|----|----|---|
| H | H | BocNH-CH(-)- (Boc-carbamate) | phenyl |
| H | H | BocHN-CH(-)- | vinyl (CH=CH$_2$) |
| H | H | BocHN-CH(-)- | -CH=CH-CH$_2$CH$_2$CH$_2$CH$_2$-N$_3$ |
| H | H | BocHN-CH(-)- | -C≡C-CH$_2$CH$_2$-N$_3$ |
| H | H | BocHN-CH(-)- | -C≡C-CH$_2$CH$_2$-NH$_2$ |
| H | H | BocHN-CH(-)- | -CH(-)-C(O)O-CH$_2$CH$_3$ |

-continued
| Y | Y' | R2 | R |
|---|---|---|---|
| | | | 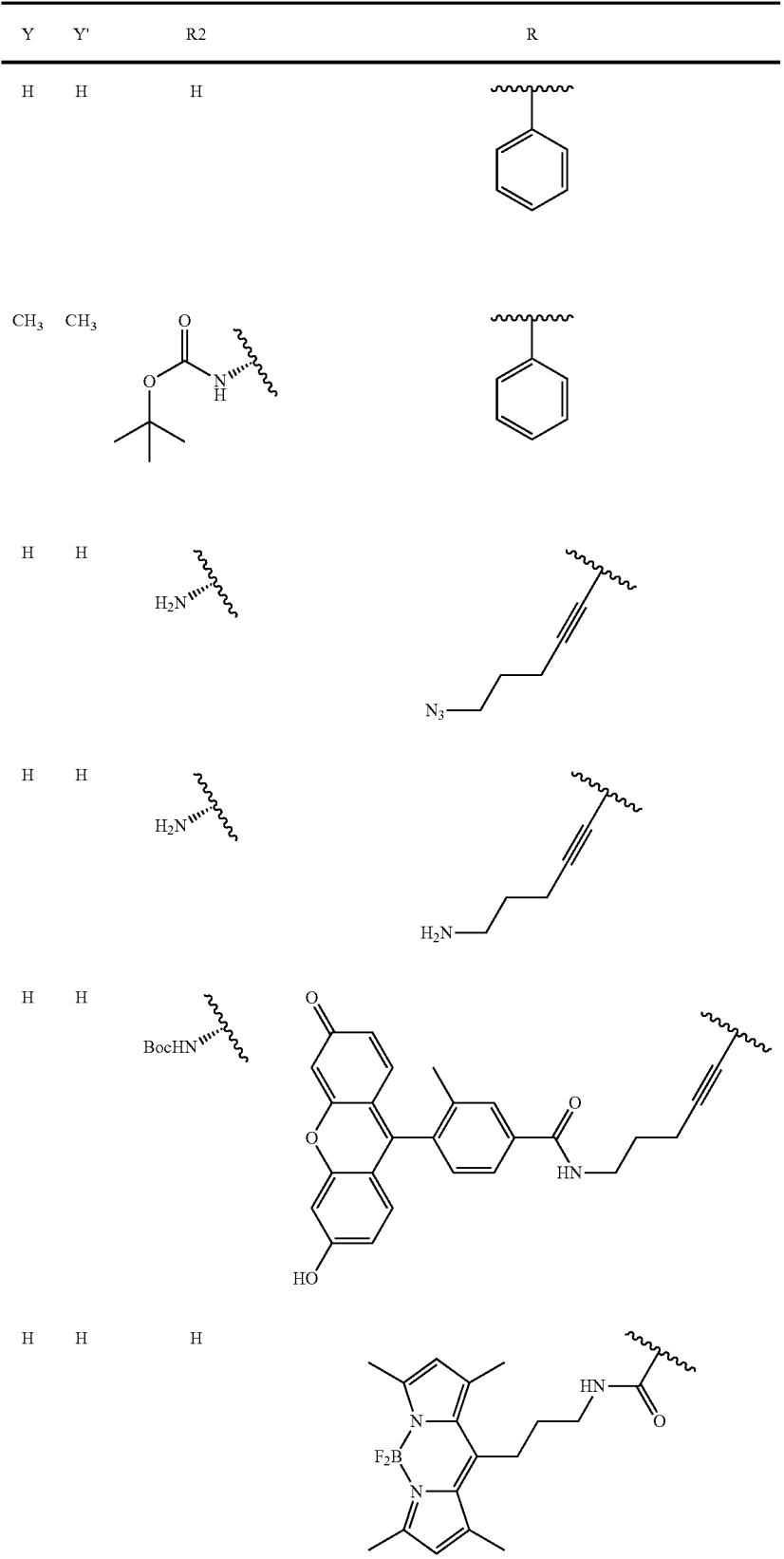 |

| Y | Y' | R2 | R |
|---|---|---|---|
| H | H | NH2 | *(structure: alkene linker-amide-N(Me)-benzamide-rhodamine dye with NEt₂ and Et₂N groups)* |
| H | H | BocHN⸺ or H | *(structure: alkyne linker-amide-desthiobiotin)* |

3. A compound according to claim 2, selected from the group comprising:

| Compound | Name |
|---|---|
| *(structure: Boc-Cys with S-benzyl sulfonium linked to 5'-deoxyadenosyl)* | (Benzyl)(5'-Deoxyadenosyl)-(N-Boc-L-Cysteine)sulfonium salt |

-continued
| Compound | Name |
|---|---|
| 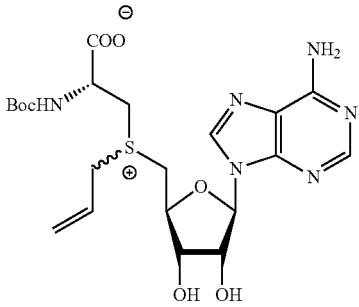 | (Allyl)(5'-Deoxyadenosyl)-(N-Boc-L-Cysteine)sulfonium salt |
| 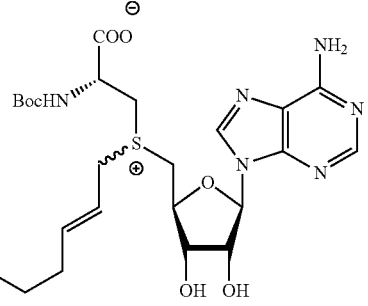 | (8-Azido-oct-2-ene)(5'-Deoxyadenosyl)-(N-Boc-L-Cysteine)sulfonium salt |
| 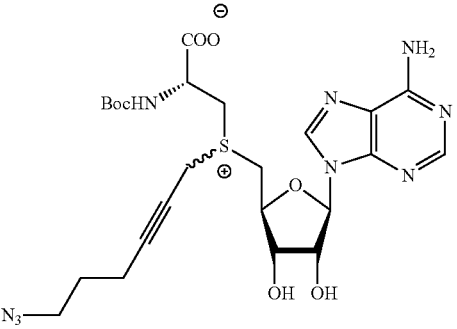 | (6-Azido-hex-2-yne)(5'-Deoxyadenosyl)-(N-Boc-L-Cysteine)sulfonium salt |
| 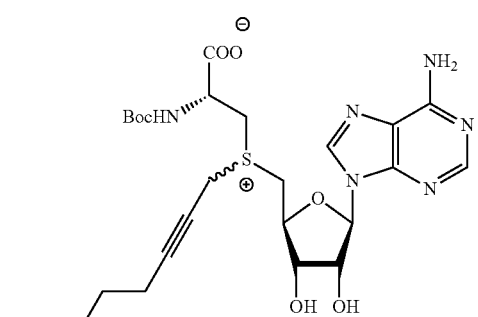 | (6-Amino-hex-2-yne)(5'-Deoxyadenosyl)-(N-Boc-L-Cysteine)sulfonium salt |
| 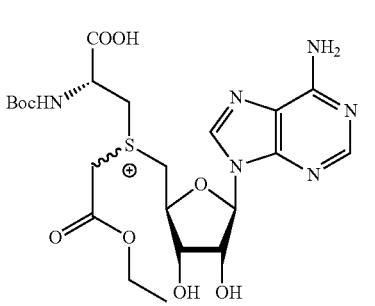 | (Ethyl Carboxymethyl)(5'-Deoxyadenosyl)-(N-Boc-L-Cysteine)sulfonium salt |

-continued

| Compound | Name |
|---|---|
| | (Benzyl)(5'-Deoxyadenosyl)-(3-Propionate)sulfonium salt |
| | (Benzyl)(5'-Deoxy-N⁶,N⁶-dimethyladenosyl)-(N-Boc-L-Cysteine) sulfonium salt |
| | (6-Azido-hex-2-yne)(5'-Deoxyadenosyl)-(L-Cysteine)sulfonium salt |
| | (6-Amino-hex-2-yne)(5'-Deoxyadenosyl)-(L-Cysteine)sulfonium salt |

-continued

| Compound | Name |
|---|---|
| | Fluorescent sulfonium salt |
| | Fluorescent sulfonium salt II |
| | Fluorescent sulfonium salt III |

| Compound | Name |
|---|---|
| (structure) | Dethiobiotin sulfonium cofactor. |

4. A compound according to claim 1, wherein said organic or inorganic anion is selected from trifluoroacetate, formate, halide and sulfonate.

5. A compound according to claim 1, wherein R additionally comprises at least one member selected from functional groups, heavy atoms or heavy atom clusters suitable for phasing of X-ray diffraction data, radioactive or stable rare isotopes, and a residue of a member selected from fluorophores, fluorescence quenchers, affinity tags, crosslinking agents, nucleic acid cleaving reagents, spin labels, chromophores, proteins, peptides or amino acids which may optionally be modified, nucleotides, nucleosides, nucleic acids which may optionally be modified, carbohydrates, lipids, transfection reagents, intercalating agents, nanoparticles and beads.

6. A compound according to claim 5, wherein said functional group is selected from an amino group, a thiol group, a 1,2-diol group, a hydrazino group, a hydroxyamino group, a haloacetamide group, a maleimide group, an aldehyde group, a ketone group, an 1,2-aminothiol group, an azido group, an alkyne group, a 1,3-diene function, a dienophilic function, an arylhalide group, a terminal alkyne group, an arylboronic acid group, a terminal haloalkyne group, a terminal silylalkyne group and a protected amino, thiol, 1,2-diol, hydrazino, hydroxyamino, aldehyde, ketone and 1,2-aminothiol group.

7. A compound according to claim 5, wherein said fluorophore is selected from Alexa, BODIPY, bimane, coumarin, Cascade blue, dansyl, dapoxyl, fluorescein, mansyl, MANT, Oregon green, pyrene, rhodamine, Texas red, TNS, fluorescent nanocrystals (quantom dots), a cyanine fluorophore and derivatives thereof and/or wherein said fluorescence quencher is selected from dabcyl, QSY and BHQ.

8. A compound according to claim 5, wherein said affinity tag is selected from peptide tags, metal-chelating groups, isotope coded affinity tags, biotin, maltose, mannose, glucose, $N$-acetylglucosamine, $N$-acetylneuraminic acid, galactose, $N$-acetylgalactosamine, digoxygenin and dinitrophenol.

9. A compound according to claim 8 wherein said peptide tag is selected from his-tags, tags with metal chelating properties, strep-tags, flag-tags, c-myc-tags, HA-tags, epitopes and glutathione or wherein said metal-chelating group is selected from nitrilotriacetic acid, ethylenediaminetetraacetic acid (EDTA), 1,10-phenanthroline, a crown ether and a HiS4-8 peptide.

10. A compound according to claim 5, wherein said crosslinking agent is selected from mono- or bifunctional platinum(ll) complexes, maleimides, iodacetamides, aldehydes and photocrosslinking agents and/or wherein said heavy atom or heavy atom cluster is selected from copper, zinc, selenium, bromine, iodine, ruthenium, palladium, cadmium, tungsten, platinum, gold, mercury, bismuth, samarium, europium, terbium, uranium, Ta6Br14, Fe4S4 and P2W-18O62 suitable for phasing X-ray diffraction data and/or wherein R comprises a nucleic acid cleaving reagent selected from the group consisting of iron-EDTA, copper-1,10-phenanthroline, acridine or a derivative thereof, an enediyne compound and a rhodium complex.

11. A complex of a compound according to claim 1 and a methyltransferase capable of using S-adenosyl-L-methionine (SAM or AdoMet) as a cofactor.

12. A complex according to claim 11, wherein said methyltransferase is capable of transferring the methyl residue of S-adenosyl-L-methionine (SAM orAdoMet) onto a nucleic acid molecule, a polypeptide, a carbohydrate or a small molecule and/or wherein said methyltransferase is an orphan DNA methyltransferase or part of a bacterial restriction modification system.

13. A complex according to claim 11, wherein said methyltransferase is selected from the group consisting of the DNA methyltransferases M.TaqI, M.HhaI, M.XbahI, M.PvuII, M.BsahI, M.FokI, M.BcnIB (M2.Bcnl), M.SssI, M.MpeI, M.PstI, M.XhoI, M.BseCI, M. M.Rsrl, M.EcoRI, or a derivative thereof.

14. A kit comprising a compound (I) according to claim 1 packed in a container.

15. The kit according to claim 14, said kit comprising the compound (I) and furthermore comprising a methyltransferase capable of using S-adenosyl-L-methionine (SAM or AdoMet) as a cofactor.

16. A kit according to claim 15, wherein said compound and said methyltransferase are packed in one or more containers and/or wherein said compound and said methyltransferase are dissolved in a buffer.

17. A pharmaceutical or diagnostic composition comprising a compound according to claim 1.

18. A method for the preparation of a modified target molecule, the method comprising the incubation of the target molecule with a compound (I) according to claim 1 in the presence of a methyltransferase which is capable of using the compound (I) as a cofactor and under conditions which allow for the transfer of part of the compounds onto the target molecule.

19. A method for detecting sequence-specific methylation in a biomolecule, comprising:
   (a) contacting a biomolecule with an S-adenosyl-L-methionine-dependent methyltransferase in the presence of a detectable cofactor of said methyltransferase; and
   (b) detecting whether the recognition site of said methyltransferase has been modified with the cofactor or a derivative thereof, wherein modification of the recognition site of said methyltransferase is indicative of an absence of methylation at said recognition site, wherein said cofactor is a compound of formula (I) according to claim 1.

20. A method for synthesizing a compound according to claim 1, the method comprising coupling a thioether with a lactone.

* * * * *